(12) United States Patent
Chou

(10) Patent No.: US 7,465,466 B2
(45) Date of Patent: Dec. 16, 2008

(54) COMPOSITIONS AND METHODS FOR PROSTATE AND KIDNEY HEALTH AND DISORDERS, AN HERBAL PREPARATION

(75) Inventor: Wen Hsien Chou, Kowloon (HK)

(73) Assignee: Integrated Chinese Medicine Holdings, Ltd., Kowloon (HK)

( * ) Notice: Subject to any disclaimer, the term of this patent is extended or adjusted under 35 U.S.C. 154(b) by 175 days.

(21) Appl. No.: 11/053,227

(22) Filed: Feb. 7, 2005

(65) Prior Publication Data

US 2005/0136140 A1 Jun. 23, 2005

Related U.S. Application Data

(62) Division of application No. 10/198,199, filed on Jul. 16, 2002, now Pat. No. 6,855,344.

(60) Provisional application No. 60/306,112, filed on Jul. 17, 2001.

(51) Int. Cl.
*A01N 65/00* (2006.01)
(52) U.S. Cl. .................................................. 424/725
(58) Field of Classification Search ...................... None
See application file for complete search history.

(56) References Cited

U.S. PATENT DOCUMENTS

| 5,665,393 | A | 9/1997 | Chen et al. |
| 6,197,309 | B1 | 3/2001 | Wheeler |
| 6,280,751 | B1 * | 8/2001 | Fletcher et al. ............. 424/401 |

FOREIGN PATENT DOCUMENTS

| CN | 1054370 | 11/1991 |
| CN | 1065489 | 10/1992 |
| CN | 1078903 | 12/1993 |
| CN | 1085785 | 4/1994 |
| CN | 1133185 | 10/1996 |
| CN | 1184659 | 6/1998 |
| CN | 1206601 | 2/1999 |

OTHER PUBLICATIONS

Ziyin et al. Journal of Traditional Medicine, 2(2), 135-140, 1982.*
Craft, N, et al., "Mechanistic concepts in androgen-dependence of prostate cancer," Cancer & Metastasis Reviews, 17(4):421-7, 1998-99 (Abstract).
Crawford, ED, "Challenges in the management of prostate cancer," British Journal of Urology, 70 Suppl 1:33-8, Nov. 1992 (Abstract).
Eisenberg, DM, et al., "Unconventional medicine in the United States. Prevalence, costs, and patterns of use," New England Journal of Medicine, 328(4):246-52, Jan. 1993 (Abstract).
Fenton, MA, et al., "Functional characterization of mutant androgen receptors from androgen-independent prostate cancer," Clinical Cancer Research, 3(8):1383-8, Aug. 1997 (Abstract).
Garnick, MB, "Prostate cancer: screening, diagnosis, and management," Annals of Internal Medicine, 118(10):804, May 1993.
Isaacs, JT, et al., "The role of androgen in the regulation of programmed cell death/apoptosis in normal and malignant prostatic tissue," Seminars in Cancer Biology, 5(5):391-400, Oct. 1994.
Jenster, G., "The role of the androgen receptor in the development and progression of prostate cancer," Seminars in Oncology, 26(4):407-21, Aug. 1999 (Abstract).
Kyprianou, N, "Induction of apoptosis in androgen-independent human prostate cancer cells undergoing thymineless death," Prostate, 25(2):66-75, Aug. 1994.
Moyad, MA, "Alternative therapies for advanced prostate cancer," Urologic Clinics of North America, 26(2):413-7, May 1999 (Abstract).
Pelletier, KR, "Current trends in the integration and reimbursement of complementary and alternative medicine by managed care organizations (MCOs) and insurance providers: 1998 update and cohort analysis," American Journal of Health Promotion, 14(2):125-33, Nov.-Dec. 1999 (Abstract).
Pelletier, KR, et al., "Current trends in the integration and reimbursement of complementary and alternative medicine by managed care, insurance carriers, and hospital providers, "American Journal of Health Promotion, 12(2):112-22, Nov.-Dec. 1997 (Abstract).
Sadar, MD, "Prostate cancer: molecular biology of early progression to androgen independence," Endocine-Related Cancer, 6(4):487-502, Dec. 1999 (Abstract).
Schulman, CC, "Prevention of prostate cancer," Scandinavian Journal of Urology & Nephrology, Supplementum, (205):50-61, 2000 (Abstract).
Tilley, WD, "Mutations in the androgen receptor gene are associated with progression of human prostate cancer to androgen independence," Clinical Cancer Research, 2(2):277-85, Feb. 1996 (Abstract).
Visakorpi, T, "In vivo amplification of the androgen receptor gene and progression of human prostate cancer," Nature Genetics, 9(4):401-6, Apr. 1995 (Abstract).
Akakura, K, et al., "Antiandrogen withdrawal syndrome in prostate cancer after treatment with steroidal antiandrogen chlormadinone acetate," Urology, vol. 45, No. 4, Apr. 1995, pp. 700-705.

(Continued)

*Primary Examiner*—Michael V Meller
(74) *Attorney, Agent, or Firm*—Blakely Sokoloff Taylor & Zafman LLP

(57) ABSTRACT

A method including contacting a prostate cell with the composition including an aliquot of the herb *Herba Epimedii*; and an aliquot of at least three supplemental herbs selected from the group consisting of *Fructus Rosae Laevigatae; Fructus Rubi; Fructus Psoralea; Radix Morindae Officinalis; Fructus Schisandrac Chinensis; Fructus Ligustri Lucidi; Semen Cuscutae*; and *Radix Astragali*. A method including identifying a subject with a prostate/kidney disorder; and establishing a regimen for administering a composition including an aliquot of the herb *Herba Epimedii*, and an aliquot of at least three supplemental herbs selected from the group consisting of *Fructus Rosae Laevigatae; Fructus Rubi; Fructus Psoralea; Radix Morindae Officinalis; Fructus Schisandrac Chinensis; Fructus Ligustri Lucidi; Semen Cuscutae*; and *Radix Astragali*.

10 Claims, 14 Drawing Sheets

OTHER PUBLICATIONS

Craft, N, et al., "A mechanism for hormone-independent prostate cancer through modulation of androgen receptor signaling by the HER-2/neu tyrosine kinase," Nature Medicine, vol. 5, No. 3, Mar. 1999, pp. 280-285.

Eisenberg, DM, et al., "Trends in alternative medicine use in the United States, 1990-1997: Results of a follow-up national survey," Journal of the American Medical Association, vol. 280(18), Nov. 1998, pp. 1569-1575.

Culig, Z, et al., "Expression, structure, and function of androgen receptor in advanced prostatic carcinoma," The Prostate, 35:63-70, 1998.

Tilley, W, et al., "Hormones and cancer: new insights, new challenges," Trends in Endocrinology & Metabolism, vol. 12, No. 5, Jul. 2001, pp. 186-188.

* cited by examiner

Pathway finder

COMPOSITIONS AND METHODS FOR PROSTATE AND KIDNEY HEALTH AND DISORDERS, AN HERBAL PREPARATION

CROSS-REFERENCE TO RELATED APPLICATION

This application is a divisional U.S. patent application Ser. No. 10/198,199, filed Jul. 16, 2002, now U.S. Pat. No. 6,855,344, which claims the benefit of the earlier filing date of co-pending provisional application Ser. No. 60/306,112, filed Jul. 17, 2001 and incorporated herein by reference.

BACKGROUND

1. Field

Presented in this application are herbal compositions and methods that provide a treatment for prostate gland and kidney disorders. In particular, a composition for the treatment or improvement of prostatitis and methods and compositions for the treatment or improvement of prostate carcinoma and relieving symptoms and improving objective signs of prostate disorders. In a further aspect, compositions and methods related to the overall health of the kidney, including the use of an herbal combination in the reduction of polyuria, incontinence, and proteinuria, as well as relieving the symptoms of these conditions. In a still further aspect, compositions and methods that improve sexual satisfaction.

2. Description of Related Art

The kidney is either one or a pair of organs in the dorsal region of the vertebrate abdominal cavity, functioning to maintain proper water and electrolyte balance, regulate acid-base concentration, and filter the blood of metabolic wastes, which are excreted as urine. Thus, the consequence of a kidney disorder can constitute an overall imbalance in the organism as a whole. Many organs such as the bladder, intestine, heart, lungs, prostate depend on the ability of the kidney to filter out the undesirable debris of the body and maintain overall homeostasis.

In Western medicine the kidneys are known to serve several vital functions, including the removal of waste from the body in the form of urine and the filtering of toxins from the blood. The kidneys also release three important hormones: (1) Erythropoietin, or EPO, which stimulates the bone marrow to make red blood cells; (2) renin, which regulates blood pressure; and (3) the active form of vitamin D, which helps maintain calcium for bones and for normal chemical balance in the body.

Kidneys are essentially blood-cleansing organs. The renal artery from the heart brings blood into the kidneys to be cleaned by a network of millions of glomerulus containing nephrons. The nephrons filter out toxins, excess nutrients and body fluid. The remaining cleaned and filtered blood then passes through the renal veins back into circulation. The filtered out material travels down a tubule that adjusts the level of salts, water and wastes that are excreted in the urine. The renal pelvis collects the urine. From the pelvis, urine travels down the ureter to the urinary bladder. The urine is expelled from, the bladder and out of the body through the urethra.

Types of kidney disease include diabetes, high blood pressure, glomerulonephritis. and cysts. Diabetes effects the body's ability to regulate glucose. Excess glucose in the blood can damage the nephrons in the kidneys reducing the blood vessels' ability to filter toxins. High blood pressure can also damage the nephrons. Glomerulonephritis generally relates to a class of other diseases not related to kidney infection.

If both kidneys stop functioning due to disease, patients experience end-stage renal disease (ESRD), or total kidney failure. Kidney failure means that the body can no longer rid itself of certain toxins and cannot properly regulate blood pressure and critical nutrients. Unless those experiencing kidney failure are treated, they can die within days due to the build-up of toxins and fluid in their blood.

The prostate gland (or prostate) is a walnut-sized, mucous-producing organ in males that lies just below the urinary bladder. The prostate typically grows and enlarges throughout life. The only known function of the prostate is to produce a secretion that nourishes and protects the sperm during reproduction. The urethra passes through the prostate gland. Hypertrophy or hyperplasia of the prostate may affect the function of the urethra, usually by occlusion of the urethra.

Prostate cancer (CaP) is the most frequently diagnosed malignancy in American males and the second leading cause of cancer death in men. Greenle et al, R. T., Hill-Harmon, M. B., Murray, T. and Thun, M. *Cancer statistics. CA Cancer J. Clin.* 51, 15-36, 2001. The most challenging aspect in the clinical management of prostate cancer is appearance of the hormone refractory state (HRPC) for which no curable therapy is currently available. Therefore, many prostate cancer patients seek alternative forms of treatment, including dietary and herbal supplements. A shortcoming in this personalized rather than physician guided disease management is a lack of sufficient scientific data on safety, functionality, and mechanisms of action of individual herbs and complex herbal formulations. HRPC often emerges as the eventual outcome of androgen deprivation therapy used to treat the androgen dependent (AD) form of prostate cancer. Aquilina, J. W., Lipsky et al., J. J. and Bostwick, D. G. *Androgen deprivation as a strategy for prostate cancer prevention. J. Natl. Canc. Inst.* 89, 689-696, 1997. Timing, modulating factors, and underlying mechanisms of AD→HRPC transition are poorly understood.

The American Cancer Society predicts that there will be about 180,000 new prostate cancer cases this year, which are estimated to contribute to 32,000 deaths. Greenlee, et al. R. T., Hill-Harmon, M. B., Murray, T. and Thun, M. *Cancer statistics. CA Cancer J. Clin.* 51, 15-36, 2001. Such statistics currently rank CaP second only to lung cancer as the leading cause of cancer death in U.S. men. Over time, however, CaP may actually exceed lung cancer as a cause of morbidity and mortality, due to an increase in adult male life expectancy and more common use of PSA screening for CaP in its early stages. Risks for CaP include unmodifiable factors such as age, race, and genetics, and modifiable factors such as diet and nutrition, occupational exposures, and possibly hormonal status. Schulman, C. C., Zlotta, A. R., Denis, L., Schroder, F. H. and Sakr, W. A. *Prevention of prostate cancer. Scand. J. rol Nephrol. Suppl.* 205, 50-61, 2000.

Features of hormone-refractory prostate cancer (HRPC). Compared to other hormone-related cancers, CaP responds readily to androgen deprivation. Sixty to eighty percent of patients with localized CaP have favorable responses to surgical and medical castration, largely due to induction of apoptosis of the androgen-dependent cells. Aquilina, J. W., Lipsky, J. J. and Bostwick, D. G. *Androgen deprivation as a strategy for prostate cancer prevention. J. Natl. Canc. Inst.* 89, 689-696, 1997. Androgen ablation, however, often leads to the expansion of androgen-independent and -hypersensitive clones. Also, even with castration, significant amounts of steroid precursors can be synthesized in the adrenal glands and are actively converted to dihydrotestosterone (DHT) by prostatic tissues. Accordingly, androgen ablation and combined androgen blockade therapies produce marginal clinical benefits for individuals with metastatic and HRPC. In these patients, the disease ultimately progresses to an androgen-independent (AI) state for which the median survival time is about 18 months and no curative therapy is currently available. Crawford, E. D. *Challenges in the management of prostate cancer. Br. J. Urol.* 70 (Suppl. 1), 33-38, 1992. This dismal clinical outcome may be attributed to a number of factors. First, even at the metastatic site, only a low percentage (<5%) of CaP cells proliferate, thus making them relatively resistant to apoptosis-restoration therapies. Lin, X., Denmeade, S. R. and Isaacs, J. T. *The genetics of programmed (apoptotic) cell death. Cancer Surv.* 25, 173-194, 1995; Isaacs, J. T., Furuya, Y. and Berfes, R. *The role of androgen in the regulation of programmed cell death/apoptosis in normal and malignant prostatic tissue. Semin. Cancer Biol.* 5, 391-400, 1994. Second, HRPC cells can proliferate in an androgen-independent manner, i.e., robust growth can occur regardless of whether normal levels of androgens are present, or if androgens are drastically diminished or even completely depleted. Sader, M. D., Hussain, M. and Bruchovsky, N. *Prostate cancer: molecular biology of early progression to androgen independence. Endocrine-Related cancer.* 6, 487-502, 1999; Fenton, M. A., Shuster, T. D., Fertig, A. M., Taplin, M. E., Kolvenbag, G., Bubley, G. J. and Balk, S. P. *Functional characterization of mutant androgen receptors from androgen-independent prostate cancer. Clin. Canc. Res.* 3, 1383-1388, 1997; Culig, Z., Hobisch, A., Hittmair, A., Peterziel, H., Cato, A. C., Bartsch, G. and Klocker, H. *Expression, structure, and function of androgen receptor in advanced prostatic carcinoma. The Prostate.* 35, 63-70, 1998. Androgen-independent proliferation of HRPC cells may relate to changes in the AR, as germline or somatic mutations and/or gene amplifications, and also to the interplay of AR with growth factors and cytokines. Cells harboring AR mutations have been reported to display altered ligand specificity, which could paradoxically switch therapeutic anti-androgens from their expected inhibitory role to potent stimulators of prostate cancer cell proliferation. Kyprianou, N., Bains, A. K. and Jacobs, S. C. *Induction of apoptosis in androgen-independent human prostate cancer cells undergoing thymineless death. The Prostate.* 25, 66-75, 1994; Akakura, K, Akimoto, S., Ohki, T. and Shimazaki, J. *Antiandrogen withdrawal syndrome in prostate cancer after treatment with steroidal antiandrogen chlormadinone acetate. Urology.* 45, 700-705, 1995]. Clonally expanded cells in HRPC may also harbor amplified and over-expressed wild-type AR gene. Schoenberg, M. P., Hakimi, J. M., Wang, S., Bova, G. S., Epstein, J. L, Fischbeck, K H., Isaacs, W. B., Walsh, P. C. and Barrack, E. R. *Microsatellite mutation (CAG24—>18) in the androgen receptor gene in human prostate cancer. Biochem. Biophys. Res. Commun.* 198, 74-80, 1994. Amplification and increased mutations of the AR, such as, expansion of CAG repeats in exon 1, changes in the ligand-binding domain and in regions flanking the AF-2 binding site, have all been reported, and shown to be present in a large percentage of HRPC specimens. Visakorpi, T., Hyytinen, E., Koivisto, P., Tanner, M., Keinanen, R., Palmberg, C., Palotie, A., Tammela, T., Isola, J. and Kallioniemi, O. P. *In vivo amplification of the androgen receptor gene and progression of human prostate cancer. Nature Genetics.* 9, 401-406, 1995; Fenton, M. A., Shuster, T. D., Fertig, A. M., Taplin, M. E., Kolvenbag, G., Bubley, G. J. and Balk, S. P. *Functional characterization of mutant androgen receptors from androgen-independent prostate cancer. Clin. Canc. Res.* 3, 1383-1388, 1997; Culig, Z., Hobisch, A., Hittmair, A., Peterziel, H., Cato, A. C., Bartsch, G. and Klocker, H. *Expression, structure, and function of androgen receptor in advanced prostatic carcinoma. The Prostate.* 35, 63-70, 1998; Jenster, G. *The role of the androgen receptor in the development and progression of prostate cancer. Semin. Oncol.* 26, 406-421, 1999; Tilley, W. D., Clarke, C. L., Birrell, S. N. and Bruchovsky, N. *Hormones and cancer: new insights, new challenges. Trends Endocrinol. Metab.* 12, 186-188, 2001; Tilley, W. D., Buchanan, G., Hickey, T. E. and Bentel, J. M. *Mutations in the androgen receptor gene are associated with progression of human prostate cancer to androgen independence. Clin. Cancer Res.* 2, 277-285, 1996. HRPC cells also show a characteristic increase in the predominance of neuroendocrine cells, interspersed among rapidly proliferating AI prostate cancer cells. Tilley, W. D., Clarke, C. L., Birrell, S. N. and Bruchovsky, N. *Hormones and cancer: new insights, new challenges. Trends Endocrinol. Metab.* 12, 186-188, 2001. Another feature of HRPC is the development of multi-antiapoptotic mechanisms, which also contribute to unabated cell growth. Tilley, W. D., Clarke, C. L., Birrell, S. N. and Bruchovsky, N. *Hormones and cancer: new insights, new challenges. Trends Endocrinol. Metab.* 12, 186-188, 2001; Tilley, W. D., Buchanan, G., Hickey, T E. and Bentel, J. M. *Mutations in the androgen receptor gene are associated with progression of human prostate cancer to androgen independence. Clin. Cancer Res.* 2, 277-285, 1996. Collectively these changes are thought to culminate in an increased sensitivity of HRPC to low concentration of androgens and growth stimulation by nonclassical ligands. Since decades are required for CaP to progress to the incurable HRPC state, this form of CaP should be readily amenable to intervention. Clinically, however, because HRPC is considered heterogeneous and complex, it is less likely to respond to single agent approaches; instead, combination and/or sequential treatment strategies may be considered more promising alternatives.

Common therapies for prostate cancer include prostastectomy, radiation, cryotherapy, and/or chemotherapy. Aquilina, J. W., Lipsky, J. J. and Bostwick, D. G. *Androgen deprivation as a strategy for prostate cancer prevention. J. Natl. Canc. Inst.* 89, 689-696, 1997; Morris, M. J. and Scher, H. I. *Novel strategies and therapeutics for the treatment of prostate carcinoma. Cancer.* 89, 1329-1348, 2000. For patients with metastatic diseases, androgen deprivation via chemical or surgical means remains the last treatment modality. Sader, M. D., Hussain, M. and Bruchovsky, N. *Prostate cancer: molecular biology of early progression to androgen independence. Endocrine-Related cancer.* 6, 487-502, 1999; Craft, N., Shostak, Y, Carey, M. and Sawyers, C. L. *A mechanism for hormone-independent prostate cancer through modulation of androgen receptor signaling by the HER-2/neu tyrosine kinase. Nature Medicine.* 5, 280-285, 1999; Craft, N. and Sawyers, C. L. *Mechanistic concepts in androgen-dependence of prostate cancer. Cancer Metastasis Rev.* 17, 421-427, 1999; Morris, M. J. and Scher H. L *Novel strategies and therapeutics for the treatment of prostate carcinoma. Cancer.* 89, 1329-1348, 2000. With passing time, however, cancer often becomes refractory to hormone ablation, leaving patients with metastatic disease no other conventional treatment options. Leewansangtong, S. and Crawford, E. D. *Maximal androgen withdrawal for prostate cancer therapy: current status and future potential. Endocrine-Related cancer.* 5, 325-339, 1998. These patients often seek unconventional "alternative" and/or "complementary" treatments, most commonly herbal therapies (phytotherapies). Such use is dramatically rising in recent years both in the U.S. and in Europe.

Eisenberg, D. M., Kessler, R. C., Foster, C., Norlock, F. E., Calkins, D. R. and Delbanco, T. L. *Unconventional medicine in the United States. Prevalence, costs and patterns of use.* N. Engl. J. Med. 328, 246-232, 1993; Angell, M. and Kassirer, J. P. *Alternative medicine—the risks of untested and unregulated remedies.* N. Engl. J. Med. 339, 839-841, 1998; Risberg, T., Lund, E., Wist, E., Kaasa, S. and Wilsgaard, T. *Cancer patients use of nonproven therapy: a 5-year follow-up study.* J. Clin. Oncol. 16, 6-12, 1998; Eisenberg, D. M., Davis, R. B., Ettner, S. L., Appel, S., Wilkey, S., Van Rompay, M. and Kessler, R. C. *Trends in alternative medicine use in the United States 1990-1997: results of a follow-up national survey.* J.A.M.A. 280, 1569-1575, 1998; Pelletier, KR., Marie, A., Krasner, M. and Haskell, W L. *Current trends in the integration and reimbursment of complementary and alternative medicine by managed care, insurance carriers and hospital providers.* Am. J. Health Promot. 12, 112-122, 1997; Moyad, M. A. *Alternative therapies for advanced prostate cancer.* Urol. Clin. North Am. 26, 413-417, 1999. The number of patients undergoing treatment with alternative medicine in the U.S. increased from 34% in 1990 to 42% in 1997. This number is still rising and there are now more visits to alternative health practitioners than total visits to all primary care physicians. Pelletier, K. R., Marie, A., Krasner, M. and Haskell, WL. *Current trends in the integration and reimbursment of complementary and alternative medicine by managed care, insurance carriers and hospital providers.* Am. J. Health Promot. 12, 112-122, 1997; Moyad, M. A. *Alternative therapies for advanced prostate cancer.* Urol. Clin. North Am. 26, 413-417, 1999; Garnick, M. B. *Prostate cancer: screening, diagnosis, and management.* Ann. Intern. Med. 118, 804-818, 1993.

Localized CaP is often treated by radical applications such as prostectomy, radiation therapy, and hormonal therapy such as androgen deprivation using physical or chemical castration. Initially, in the majority of patients receiving such forms of therapy there is a response, but frequently this response is followed by establishment and expansion of hormone-insensitive and refractory clones. The establishment of such states is often rapidly followed by the recurrence of disease, and metastasis to sites beyond the confines of the gland. Emergence of metastatic prostate cancer, even if detected early, is not readily treatable. Thus, what are urgently needed are new easily compliant preventative and treatment measures. Further, research directed towards mechanistic understanding of newly developed treatment modalities is also imperative.

Significant geographic variations and marked differences among various ethnic/racial groups with respect to the age-adjusted incidence and mortality rates for clinical CaP have been observed in epidemiological studies; both environmental and genetic factors and their interplays are hypothesized to contribute to the observed variable incidence. In particular, the possible involvement of diet capable of exerting promoting or protecting influences on the progression and establishment of clinically important prostate cancer have been proposed. An alternative explanation for the observed varied incidence of clinical CaP is that culture specificity and diversity, exemplified by food and other lifestyle preferences, maintain potentially metastatic CaP in a latent state.

The multi-factorial, multi-stage nature of carcinogenesis underscores the heterogeneous and complex nature of cancer. The heterogeneity and complexity of cancer presents immense obstacles and challenges to scientists and clinicians, with respect to better understanding and clinical management of cancer. Increasingly, it is recognized that the single agent approaches, which have been traditionally and broadly applied to the treatment of malignant diseases, are inadequate for treatment. Accordingly, concerted efforts have been mounted to better strategize combination and/or sequential therapies for treating a variety of tumors.

Herbal therapies may be considered a form of combination therapy. They differ from the single agent approach in that aggregate bioactive, inactive, and counter-active agents are present. The collective effect of these agents typically results in reduced toxicity, and appearance of new and novel activities. The combination of activities present in herbal therapies can be important determinants in cancer prevention/treatment since they may circumvent overlapping molecular pathways that may result in successful cancer treatment.

SUMMARY

In one embodiment, a composition of herbs is delivered to a target system or organ as a modular unit including a cocktail of bioactive, inactive, and counter-active chemical ingredients manifesting a broad spectrum of biological activities, and hence are more effective compared to a single herb, with its more limiting chemical profile. This embodiment is in line with the basic concepts of traditional Chinese medicine, which espouses that functionality and efficacy of herbal formulations rely on strategic combination of different ingredients to potentially generate synergistic or novel activities.

In contrast to Western countries, in eastern Asia, particularly in China, herbal therapies have been common throughout centuries. For some diseases, Chinese herbal therapies may increase the effectiveness of modern drug treatments, reduce their side effects, and under the best circumstances replace them completely. Little of the knowledge developed by practitioners of phytotherapy in Asia, however, has been relayed to Western medicine and there is little comprehension among the Western medical establishment of the possibilities that herbal medicine can offer.

The incidence of CaP has increased significantly in recent decades in the U.S. Therapies for newly diagnosed, localized CaP such as prostatectomy and hormonal ablation offer reasonable success because the cells at this stage respond to and are dependent on androgens. For advanced CaP, the cells are refractory to androgens; as a result, no life-extending cure currently exists. More effective prevention and control of prostate carcinoma therefore requires the identification of novel agents capable of modulating the growth of both AD and HRPC. Because of lack of life-prolonging therapies for HRPC, patients actively seek alternative forms of treatment, including the use of herbal supplement.

A composition of herbs and their extracts which, based on in vitro studies using prostate cancer cell lines mimicking the sub-clinical, hormone-responsive, and the advanced, hormone-refractory states of prostate carcinoma which are useful and applicable in the treatment of prostate carcinoma and which can also be used as a dietary supplement is disclosed. The combination of herbs and their extracts profoundly reduce the expression of PSA and NFκB (nuclear factor kappa B), effectively suppress cell proliferation, and almost completely abolish the ability of prostate cancer cells to form colonies. In addition, the in vitro studies using prostate androgen-responsive LNCAP cell show that extracts of a composition of multiple herbs down-regulates NFκB whose expression is known to be involved in cell survival. In addition, volunteers who have personally administered one of the herbal composition over varied time periods have seen remarkable improvements to their symptoms.

A composition of herbs and methods related to the overall health of the kidney, including the use of the herbal combination in the reduction of polyuria, incontinence, and proteinuria, as well as relieving the symptoms of these conditions is also disclosed. Beneficial effects can include the elimination or improvement of lower urinary tract symptoms by reducing prostate inflammation and urethra compression due to a swollen prostate. This alleviation could prevent the need for inappropriate prostate surgery. Thus, a non-surgical option would be provided. This could lead to prostate cancer prevention, improvement in the frequency and strength of the urine stream and reduction of PSA. In a still further aspect, compositions and methods that improve sexual satisfaction are disclosed.

Embodiments relate to compositions and the use of these compositions as agents for the treatment of cancer and other disorders of the prostate and kidney. The compositions include combinations or sub-combinations of components derived from *Herba Epimedii* (xianlingpi), *Radix Morindae Officinalis* (Bajitian), *Fructus Rosae Laevigatae* (Jinyingzi), *Fructus Rubi* (Fupenzi), *Fructus Schisandrac Chinensis* (Wuweizi), *Fructus Ligustri Lucidi* (Nuzhenzi), *Semen Cuscutae* (Tusizi), *Fructus Psoraleae* (Buguzhi), and *Radix Astragali* (Huangqi). In one embodiment, a therapeutically effective amount of the composition is administered to an individual in need of treatment. In another embodiment, a prophylactically effective amount of the composition is administered to an individual. In still another embodiment, the compositions are administered in effective amounts to maintain the health of an individual.

BRIEF DESCRIPTIONS OF THE DRAWINGS

The following drawings form part of the specification and are included to further demonstrate certain aspects of the embodiments. The application may be better understood by reference to one or more of these drawings in combination with the detailed description of specific embodiments presented herein.

Figure 5:
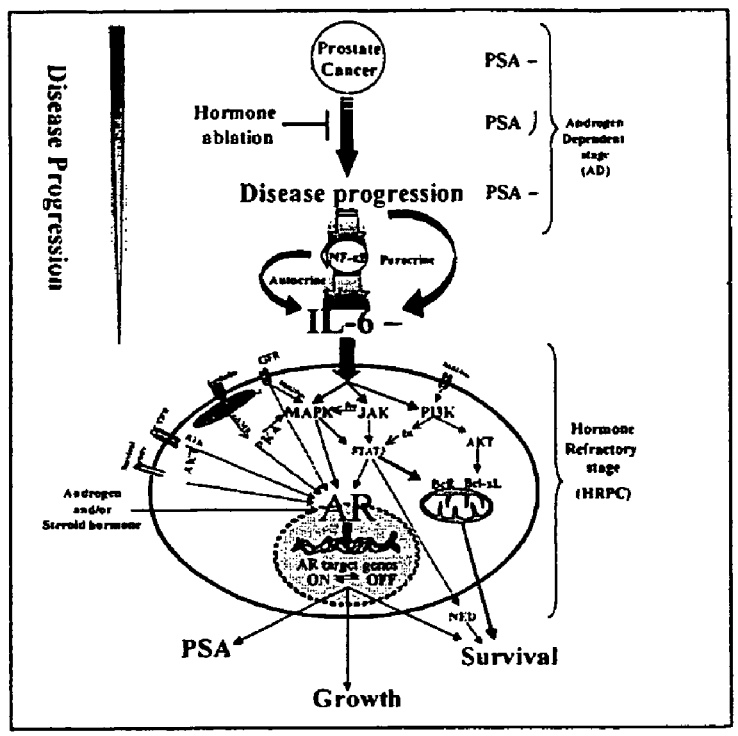

FIG. 5 schematically illustrates the involvement of IL-6 in the control of PSA expression, cell growth, and survival in human prostate cancer cells.

Figure 6:
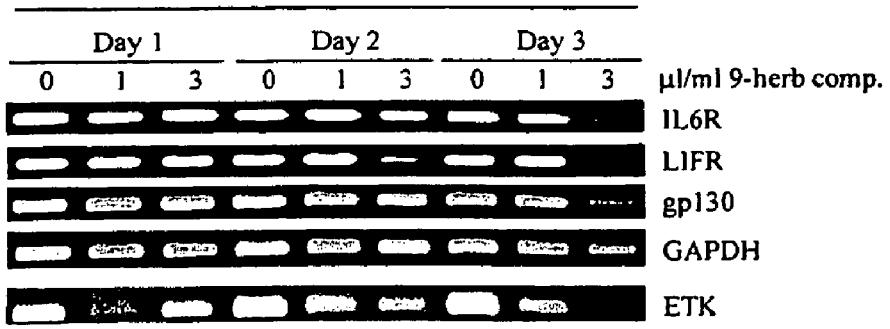

FIG. 6 illustrates the expression of certain genes in LNCaP cells in response to embodiments of the composition.

Figure 7:
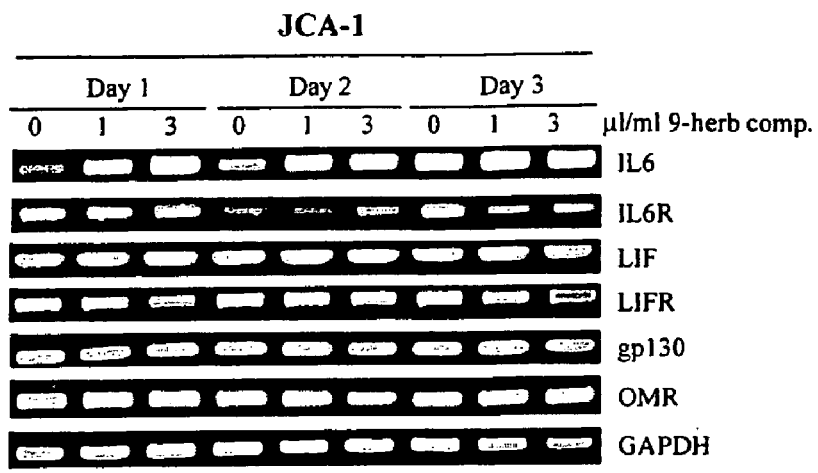

FIG. 7 illustrates the expression of certain genes in JCA-1 cells in response to embodiments of the composition.

Figure 8:
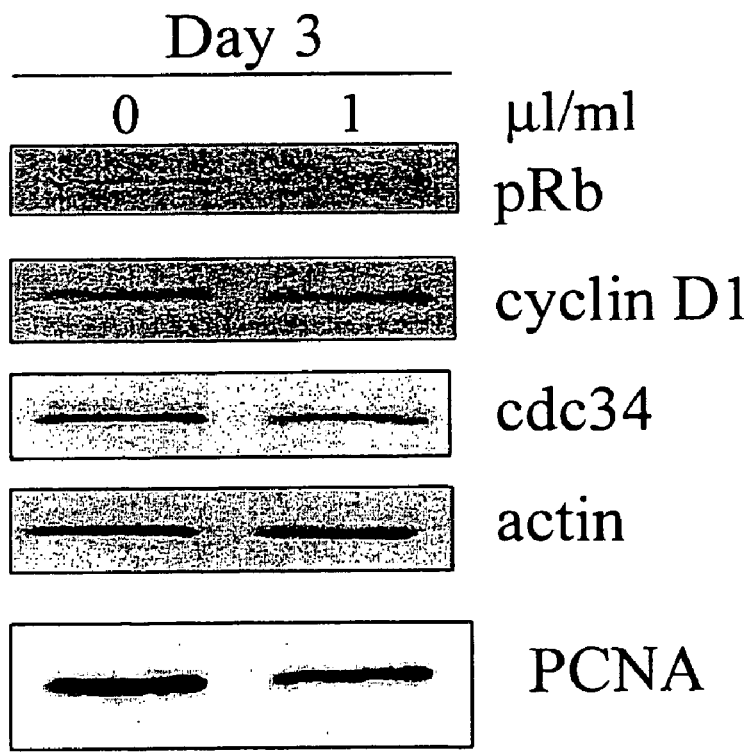

FIG. 8 illustrates the presence or absence of regulatory molecules after exposure of LNCaP cells to an embodiment of the composition.

Figure 9:
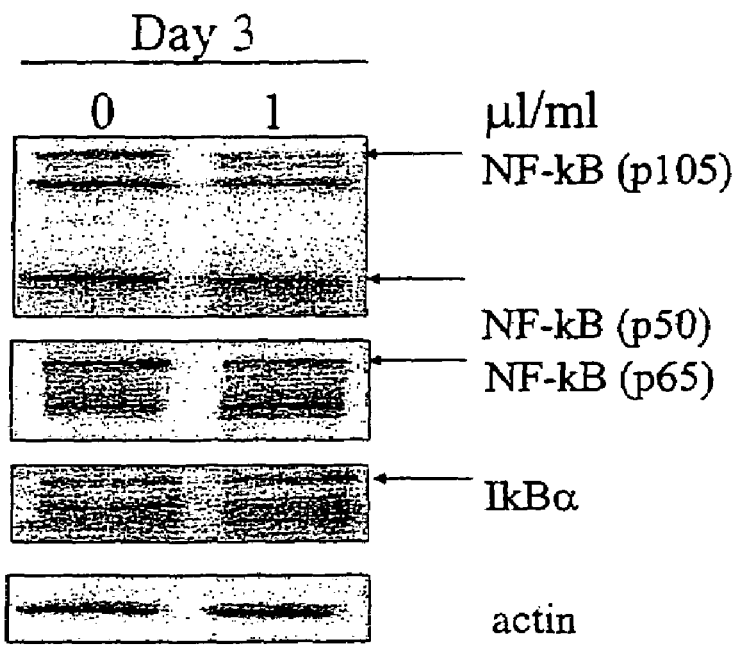

FIG. 9 illustrates the presence or absence of NFκB after exposure of LNCaP cells to an embodiment of the composition.

Figure 10:
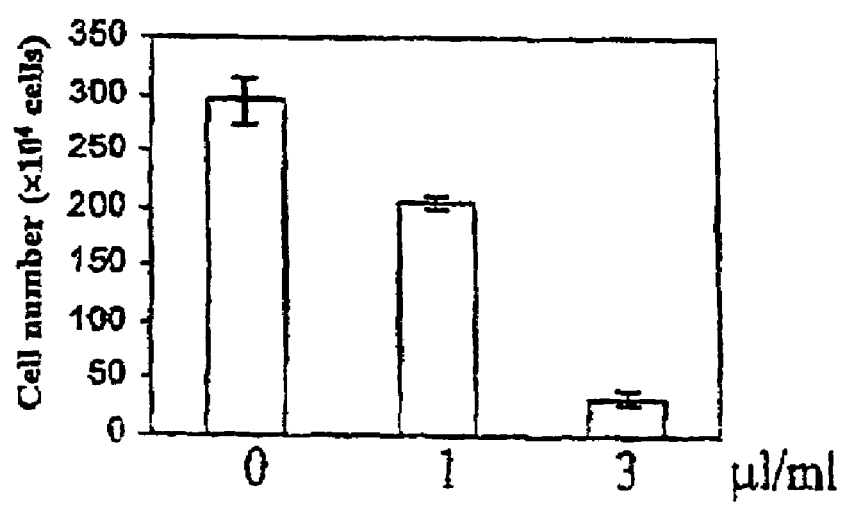

FIG. 10 illustrates the proliferation of DU-145 cells in response to embodiments of the composition.

Figure 11:
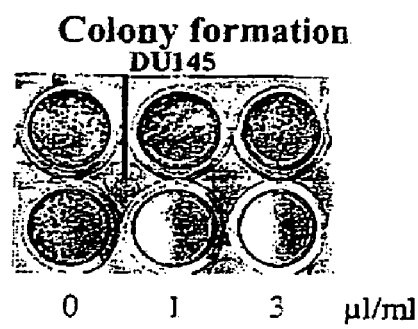

FIG. 11 illustrates the colony-forming ability to DU-145 cells in response to embodiments of the composition.

Figure 12:
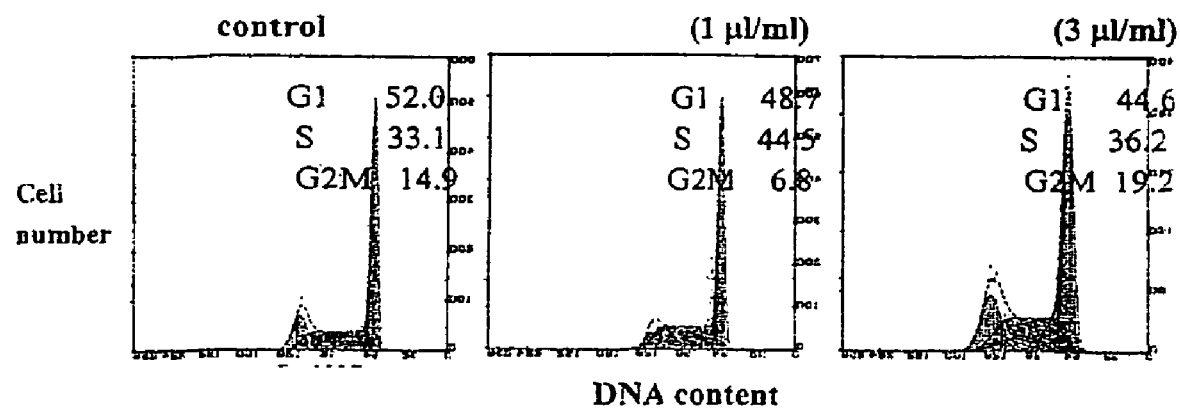

FIG. 12 illustrates the DNA content of DU-145 cells cultured in embodiments of the composition.

Figure 13:
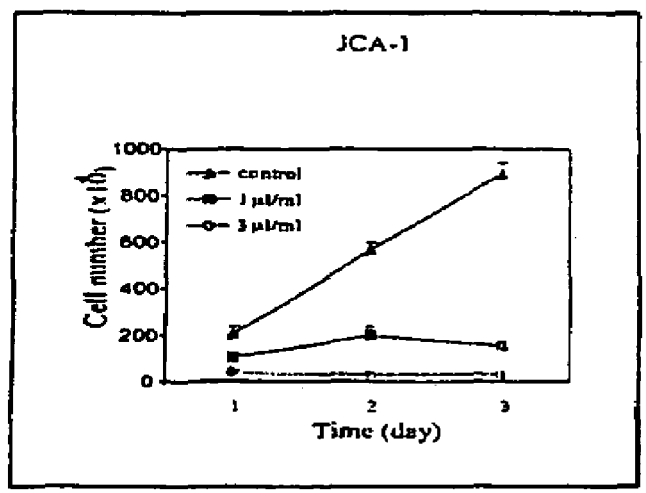

FIG. 13 illustrates the inhibition of JCA-1 cell proliferation by embodiments of the composition.

Figure 14:
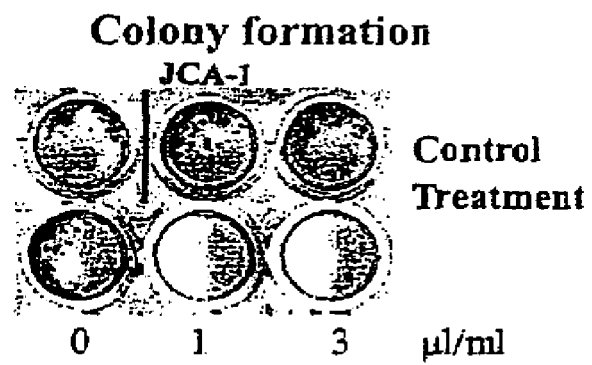

FIG. 14 illustrates the clonogenicity of JCA-1 cells to embodiments of the composition.

Figure 15:
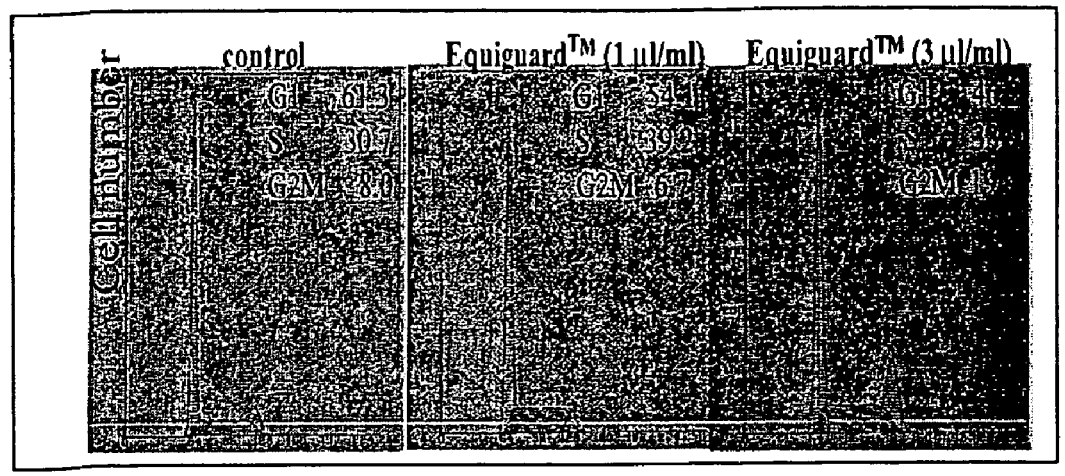

FIG. 15 illustrates the DNA content of JCA-1 cells cultured in embodiments of the composition.

Figure 16:
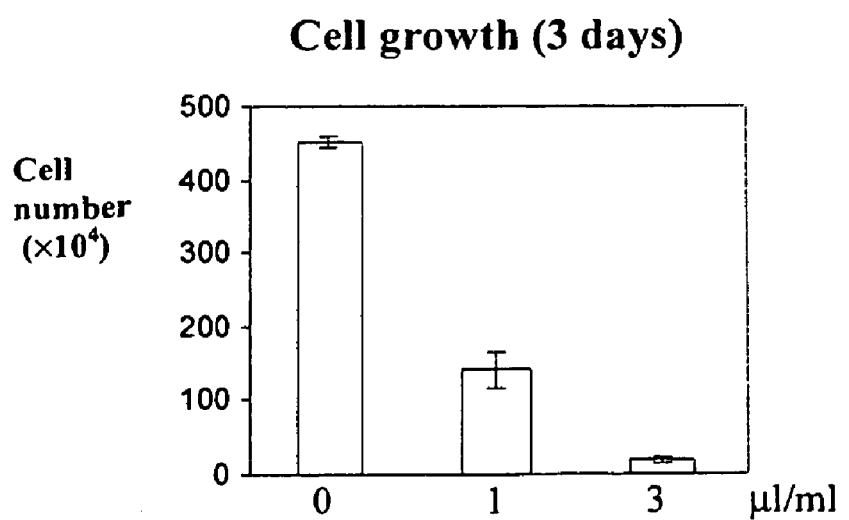

FIG. 16 illustrates growth inhibition of PC-3 cells by embodiments of the composition.

Figure 17:
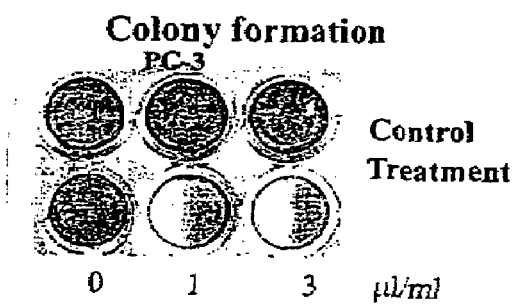

FIG. 17 illustrates the clonogenicity of PC-3 cells to embodiments of the composition.

Figure 18:
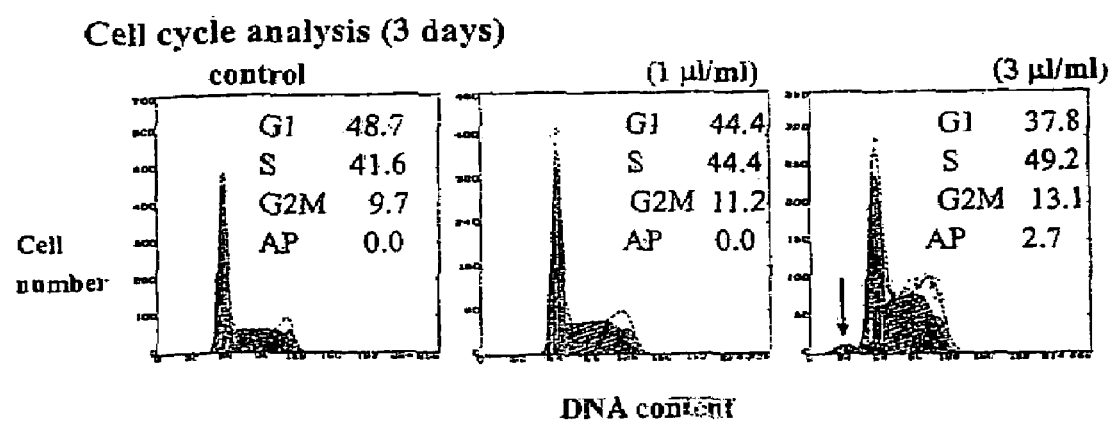

FIG. 18 illustrates the DNA content of PC-3 cells cultured in embodiments of the composition.

Figure 19:
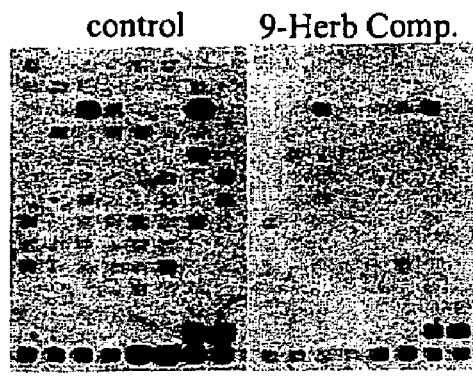

FIG. 19 illustrates array analysis of gene expression of a control and an embodiment of the composition.

Figure 20:
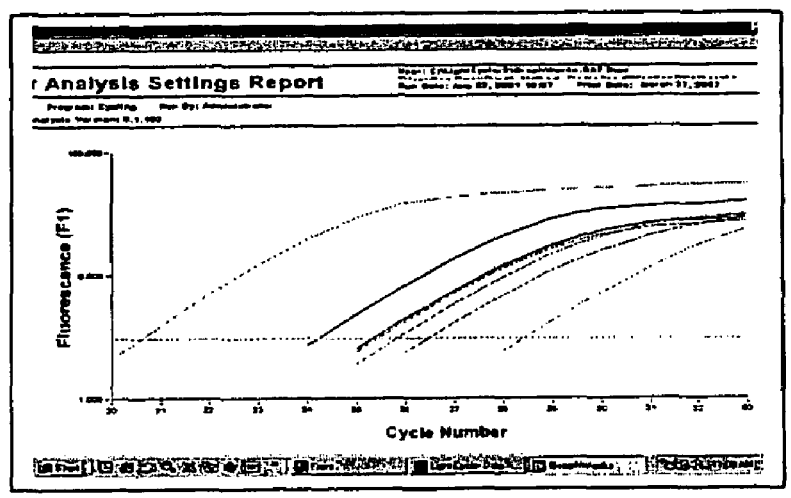

FIG. 20 illustrates an analysis of gene expression using real-time PCR of an embodiment of the composition.

Figure 21:
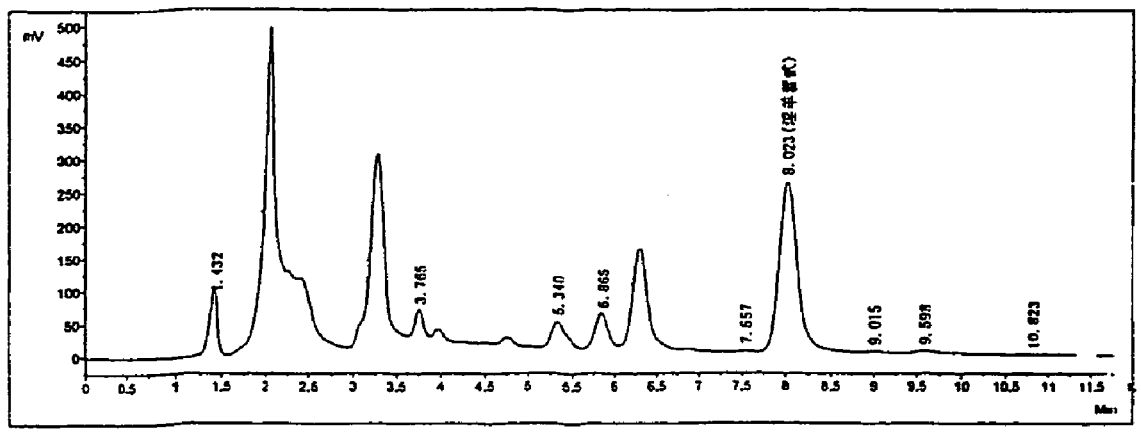

FIG. 21 illustrates high performance liquid chromatography (HPLC) data for icarrin in a sample of an embodiment of the composition.

Figure 22:
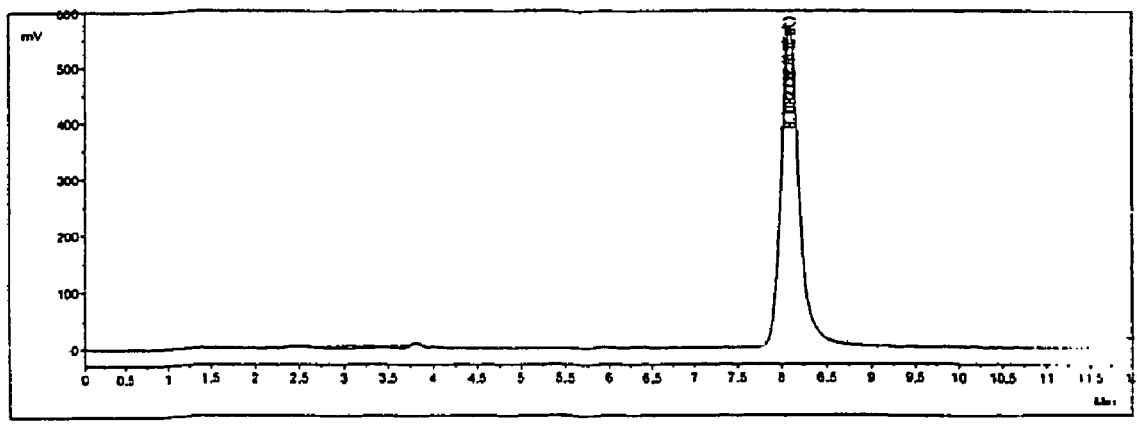

FIG. 22 illustrates HPLC data for icarrin in a standard sample.

Figure 23:
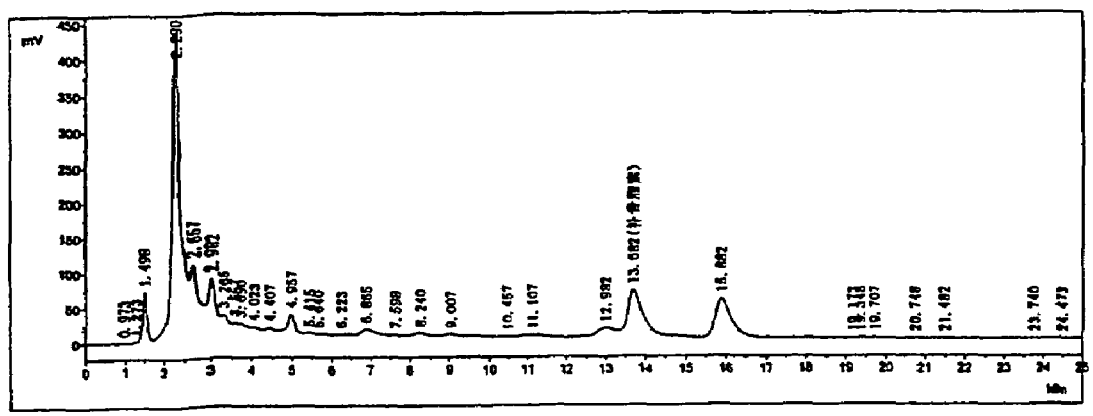

FIG. 23 illustrates HPLC data for psoralen in a sample of an embodiment of the composition.

Figure 24:
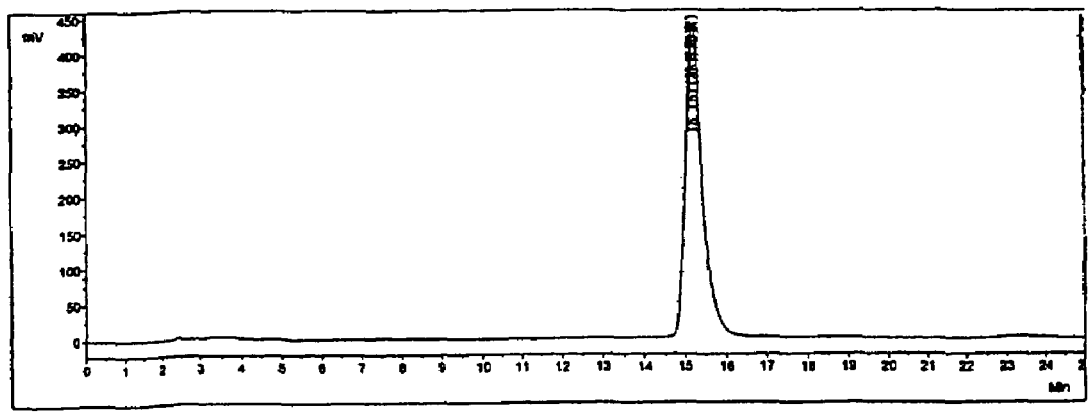

FIG. 24 illustrates HPLC data for psoralen in a standard sample.

Figure 25:
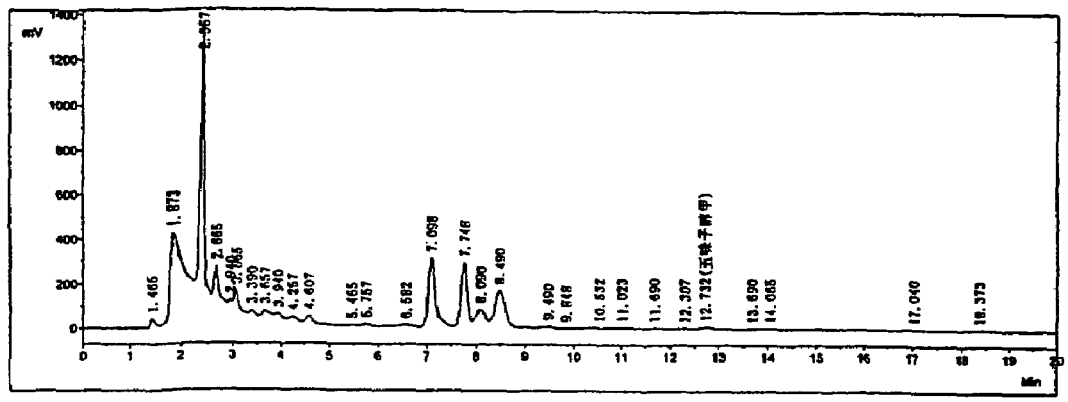

FIG. 25 illustrates HPLC data for schizandrin in a sample of an embodiment of the composition.

Figure 26:
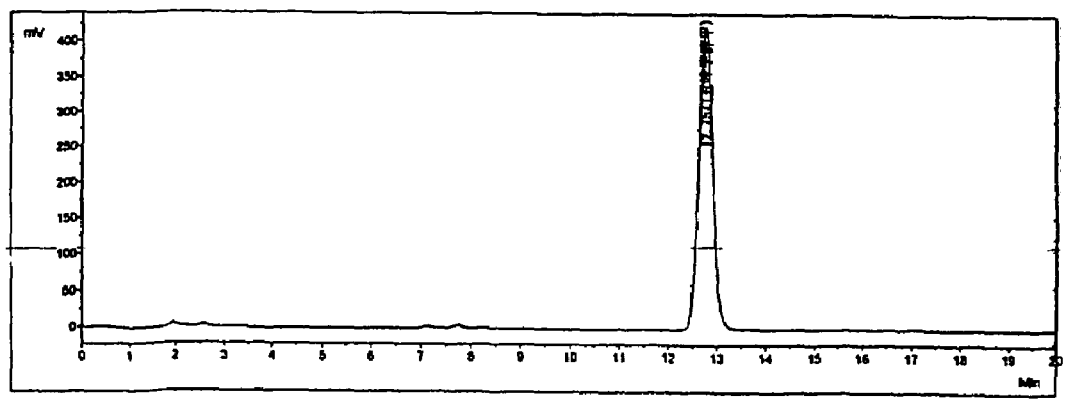

FIG. 26 illustrates HPLC data for schizandrin in a standard sample.

Figure 27:
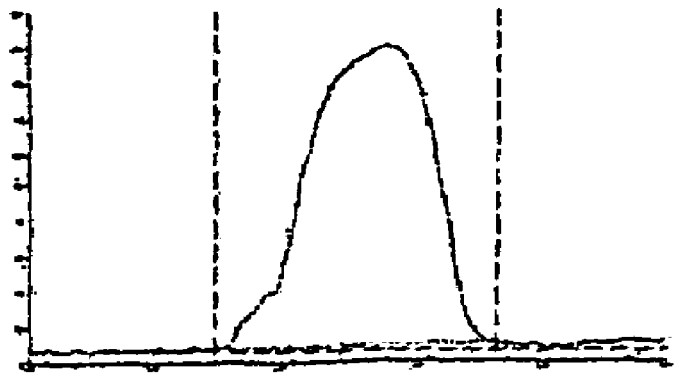

FIG. 27 illustrates thin layer chromatography (TLC) data for oleanolic acid in standard sample.

Figure 28:
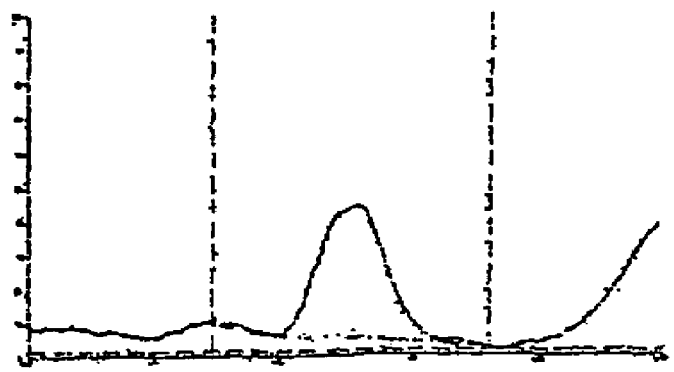

FIG. 28 illustrates TLC data for oleanolic acid in a sample of an extract of the herb *Fructus Ligustri Lucidi*.

Figure 29:
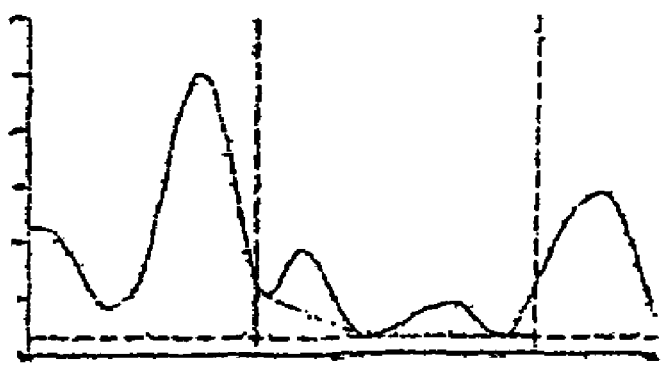

FIG. 29 illustrates TLC data for oleanolic acid in a sample of an embodiment of the composition.

DETAILED DESCRIPTION

Chinese Medicine

In Chinese or Eastern medicine, the kidneys constitute one of the most important organs in the body. Traditionally, kidneys are described as the vaporizing power of the body. The kidneys are able to separate "clear" and "turbid" water. Turbid water is excreted by the kidneys through the bladder as urine. But, "clean" water is sent back to the lungs where it can be distributed to the entire body. Similar to Western medicine, Chinese-medicine views the kidney as a water-balancing organ. The kidney helps to grasp "natural air qi" (vital energy), where qi is inhaled by the lungs for the body to use it. If the kidneys malfunction, respiratory conditions occur such as shallow breathing, coughing and wheezing. Jing is an essential life essence that is inherited from the mother and father. It is needed for reproduction, growth and development, and maturation. As jing declines, the body starts to age. Jing is responsible for bone marrow that is subsequently responsible for bone growth. This jing comes from the kidney. If jing is deficient, then soft bones occur and problems with bones and teeth result. The kidneys help transform jing into blood. This is viewed as nourishment to the blood via the kidneys. This is considered equivalent to the production of erythropoeitin in Western medicine whereby the production of red blood cells is stimulated in the bone marrow. In Chinese medicine, every organ has an external opening to the outside. The kidneys open through the ears and sexual organs. Problems such as ringing in the ears or erectile disfunction are considered problems with the kidney.

Urinary incontinence is the loss of ability to control urination. The loss of control is generally related to the muscles that control the bladder. Polyuria is viewed as the kidneys inability to concentrate the urine, which results in large amounts of urine being produced. In Chinese medicine, polyuria is viewed as a jing and qi deficiency. Therefore, the kidneys loose their astringent properties that transpires to their ability to hold or store urine resulting in polyuria. Urinary incontinence is thought to be the inability to transform qi. The bladder requires successful qi transformation in order to control urination. Eastern medicine has looked to herbal applications in order to maintain or regenerate the balance of the kidney system.

Traditionally, in Chinese medicine, there is no understanding of a separate prostate organ. The Chinese classify the prostate as part of the kidney system. It is also thought that the kidneys are responsible for sexual function. If the kidney is not functioning properly then impotence in males and infertility, pregnancy and menstruation problems and leucorrhoea in women can occur. It is believed that excessive sexual activity causes depletion of stored jing and this is when problems can occur.

Prostate cancer in Chinese medicine is described according to its symptoms. The causes are related to depletion of kidney essence. This is caused by testosterone and estrogen metabolism disorders. Chinese medicine that relates to the functioning of the organs in the lower abdomen refers dampness, heat and evil accumulation in this region. The source of dampness is externally introduced (intake of greasy foods) and also can be generated form an organ itself that is malfunctioning. The dampness is thought to eventually cause inflammation and mutation of the cells that formulate cancer. In addition, when blood stasis is interrupted, toxins build up which can also cause cancer. Therefore the kidney system and subsequently the prostate organ must be properly maintained.

Traditional Chinese medical ("TCM") practices approach the treatment of diseases using a "holistic/integrative" philosophy embodying several distinct features. Contrary to the "pharmaceutical" approaches of isolating, characterizing and applying the most potent of the active principles in a mixture, the "integrative" strategy emphasizes application of the total spectrum of bioactive ingredients present in a herbal mixture and evaluates success based on the "well being/curing" of the patients as a whole. Second, Chinese herbal formulations often comprise mixtures of herbs and thus rely on "group" administration of bioactive agents to affect cellular proliferation, restore apoptosis, and regulate prostate specific gene expression, while exerting minimal, sub clinical toxicity, in target cells. Such an approach is not predicated on information involving the pathways leading to development of a particular form of malignancy.

In Chinese medicine, *Epimedium* is used to treat cancer that relates to kidney yang deficiency. It is usually used together with *Radix Aconiti Praeparata, Rhizoma Curculiginis, Radix Morindae Officinalis, Fructus Psoraleae* and *Rhizoma Polygonati* to treat chorionic epithelial cancer. *Epimedium* can also be used with *Radix Aconiti Praeparata, Rhizoma Curculiginis, Fructus Trichosanthis, Semen Armeniacae Amarum* and *Rhizoma Pinelliae* to treat lung cancer of yang deficient and phlegm-damp type. The later formula has been studied in a clinical study of 100 lung cancer patients, the total effective rate was 62.2%. *Epimedium* has also been used with heat-clearing herbs like *Flos Loincerae, Radix Rhapontici, Herba Taraxaci*, "Di Ding" or with "Hong Shen", *Radix Polygoni Multiflori, Cemucervi Pantotrichum, Radix Polygoni Multiflori* to treat leukemia. A previous study using these two formulas to treat 28 leukemia patients resulted in 17 patients completely recovering. The total effective rate was 85.7% and the longest survival time was 3 years and 2 months. While using with *Flos Loincerae, Herba Taraxaci, Radix Pulsatillae* and *Cortex Phellodendri, Rhizoma Alismatis, Concha Ostreae, Rhizoma Zedoariae, Epimedium* can be used to treat colon and pancreatic cancers respectively.

TCM understanding of the kidney is much more extensive than the western anatomical kidney; it is an important organ that is central to a series of functions. The kidney stores primordial yin and primordial yang which are attributive to water and fire of body respectively, TCM regards the kidney as the root of life and origin of native constitution. The major physiologic functions include: storage of the essential qi of organs and the essential-fluid for reproduction; domination of the production of bones and marrow substance, marrow nourishes the brain and improves intelligence; governing of water by controlling the opening and closing of water gate and engaging in metabolism of body fluid; Grasping qi (the kidney is the root of qi); kidney-qi communicates with ears and controls hearing; controlling the opening and closing of stomach; cooperating with the bladder; essence will be manifested by healthy hair and bones.

Essence can be considered as the underlining of all aspects of organic life. It is the material basis for all kinds of functional activities, and growth and development of human body. Essence is stored in kidney. In addition, it also manifests as a function of human vitality. The stored essence includes congenital jing (also called congenital essence) and acquired jing (also called acquired essence).

Congenital jing determines the constitution and characteristics that a person will take through life. After birth, the congenital jing is nourished by the acquired jing, and gradually becomes the material basis for development and reproduction. Thus, it is also named as "reproductive jing."

Acquired jing: Also named as "jing of organs" because this jing irrigated through the organs. It is obtained from ingested foods and fluids through the action of the spleen and stomach. After birth, the ingested food nutrition transfers into nutrient substances in stomach, and these substances are further transformed into nutrient jing by the spleen.

This nutrient essence is mainly responsible for irrigating and nourishing the organs. Therefore the acquired jing is equivalent to nutrient jing or jing of organs. In order to maintain the functions of the organs, the acquired jing provides daily supplement to them, but the excessive portion will store in kidneys which is used for nourishing the organs on demand. This result in the way that the acquired jing circulate repeatedly in the kidney; excessive portion stores inside in one way, and send out for supplying the extra demanded in the other way. Thus, the kidney also stores the jing of organs.

Although the above two jing are from different sources, they both return to the kidney. The kidneys play an important role in water movement and balance of the whole body. It vaporizes the fluid. By vaporization, the nutrient fluid can be distributed through out the body, and the organs' metabolized and waste fluid can be excreted. This type of regulation of body fluid is also named as "opening and closing of the gate of water."

Under balanced conditions, the kidney regulates normal metabolism of body fluid such as urination. When kidney-yin and kidney-yang are unbalanced, opening and closing of the gate of water will be abnormal and metabolism of body fluid is disturbed. In case of yang-deficiency and yin-excessive, the incidences of closing are much more than opening, which lead to problems in production and excretion of urine, resulting in scanty urine and edema. But if there is yin-deficiency and yang-excessive, incidences of opening are much more than closing, problems like polyuria will appear. Besides, the roles that are played by the lung, spleen and bladder during the metabolism of body fluid, are all depend on the vaporization function of kidney to motivate. Therefore, in the metabolism of body fluid, kidney-yang's vaporization control on opening and closing the gate of water is a crucial segment for balancing fluid metabolism.

Herbal Compositions

As described herein, groups of herbs can be chosen and combined according to their biological activities. Each herbal component selected in this group is known, but their combination or sub-combinations are a new concept. As a holistic approach to combating prostate cancer, herbs can be selected for particular activities such as anti-tumor activity; immune stimulating activity; anti-viral/bacterial activity; anti-inflammatory activity; and/or anti-benign prostate hyperplasia biological activity. Most of the herbs can have multiple activities. When combined according to the teachings described herein, a composition provides synergistic benefits/results toward the treatment of disorders or health of the kidney system. In one embodiment, the composition is a dietary supplement formulated to restore stasis in the kidney, that, according to traditional Chinese medicinal concepts is involved in regulating and maintaining balance of the entire urological system.

Certain embodiments use a plurality of herbs and/or herbal extracts to manufacture an herbal composition. One embodiment provides a composition of approximately nine herbs and their extracts which, based on studies, described herein, are useful for the treatment or improvement of prostate disorders, preferably prostate carcinoma. In other embodiments, the compositions can be used as dietary supplements for prophylaxis of prostate disorders and for promotion of prostate health. In another embodiment, the compositions may be administered to reduce the expression of PSA, effectively suppress cell proliferation, and/or inhibit the colony forming ability of prostate cells that are cancerous, hypertrophied, hyperproliferative, or involved in prostatitis.

Alternate embodiments include the treatment of other hyperproliferative disorders and cancers. The growth inhibitive effects are exemplified in the prostate cancer model and can be extrapolated to other proliferative disorders, especially hormone dependent proliferative disorders. Proliferative disorders that may be treated by embodiments include, but are not limited to cancers; arthritis, stenosis of coronary vessels, cancers of the breast, testicle, lung, liver, kidneys, prostate, brain, bone, blood, and other tissues. Embodiments also relate to compositions and the use of these compositions in a prophylactic manner to benefit the overall health of the prostate and kidney and to improve sexual satisfaction.

The composition may be a combination or sub-combination of the following herbs *Herba Epimedii* (xianlingpi) or *Herba epimedium brevicornum Maxim* (stem and leaves), *Radix Morindae Officinalis* (Bajitian), *Fructus Rosae Laevigatae* (Jinyingzi), *Fructus Rubi* (Fupenzi) or *Rubus chingii* Hu (fruit), *Fructus Schisandrac Chinensis* (Wuweizi) or *Schisandra chinensis* (Turz) Baill (fruit), *Fructus Ligustri Lucidi* (Nuzhenzi) or *Ligustrum lucidum* Ait (fruit), *Semen Cuscutae* (Tusizi) or *Cuscuta chinensis* Lam (seed), *Fructus Psoraleae* (Buguzhi) or *Psoralea corylifolia* L. (fruit), and *Radix Astragali* (Huangqi) or *Astragalus membranaceus* [Fisch.] Bge(root). Pinyin names are listed in parenthesis following the first Latin name of the herb or plant. Lyophilized powders of herbal extract can be purchased from a variety of vendors such as the Shanghai Medical College of Traditional Chinese Medicine, Shanghai, China. In one embodiment, the composition includes an aliquot of the herb *Herba Epimedii* and an aliquot of one or more of the supplemental herbs *Radix Morindae Officinalis, Fructus Rosae Laevigatae, Fructus Rubi, Fructus Schisandrac Chinensis, Fructus Ligustri Lucidi, Semen Cuscutae, Fructus Psoraleae*, and *Radix Astragali*. In another embodiment, the composition includes an aliquot of the herb *Herba Epimedii* and an aliquot of at least three of the supplemental herbs. In still another embodiment, the composition includes an aliquot of a portion of all nine listed herbs.

TABLE 1

HERBS

A. *Herba Epimedii* (stem and leaves)

*HERBA EPIMEDII*, or commonly known as *Epimedium*, is the dried, aerial stem and leaves of *Epimedium sagittatum* (Sieb. Et Zucc.) Maxim or *E. brevicornum* Maxim. The plant is harvested in the summer and autumn seasons. It can be found in the interior regions of China such as the Shanxi, Anhui, ands Henan provinces.
SCIENTIFIC NAMES: *Epimedium acuminatum*; *E. sagittatum*; *E. brevicornum*; *E. grandiflorum*; *E. koreanum*; *E. pubescens*; *E. sagittatum*; *E. wushanese*; and other *Epimedium* species.
FAMILY: Berberidaceae.
ALSO KNOWN AS: Xian Ling Pi, Yin Yang Huo, Barrenwort, Horny Goat Weed, Japanese *Epimedium*.
CHINESE USES: Reinforces the kidney-yang, strengthens the bones and tendons, and relieves rheumatic conditions.
ADDITIONAL USES: Kidney deficiency manifested as impotence, premature emission, enuresis, frequent urination, weakness and degeneration of knee and loin, sterility, dizziness, palpitation, fatigue, and amnesia.
Rheumatic conditions caused by wind and dampness manifested as arthralaia, numbness, muscular spasm and weakness of limbs, and infantile paralysis. It is used for cardiovascular diseases such as coronary heart disease, hypertension, and angina. Eliminates phlegm and relieves chronic cough and asthma, especially those of the yang-deficiency type.
SIDE EFFECTS: It is safe to take orally in moderate amounts. Suggest avoid using during pregnancy and lactation, as there is insufficient reliable information available.
It may result in dizziness, vomiting, dry mouth, thirst, and nosebleed.
B. *Fructus Rosae Laevigatae* (fruit)

*FRUCTUS ROSAE LAEVIGATAE* is more commonly known as the fruit of the Cherokee Rosehip. The form used in traditional Chinese medicine is the dried, ripe fruit of Rose

TABLE 1-continued

HERBS

*laevigata Michx.* It is collected during October and November when the fruit ripens to a red color. The plant grows in China in the Guangdong, Guangsi, and Zhejiang provinces.
SCIENTIFIC NAMES: *Fructus Rosae Laevigatae*.
FAMILY: Rosaceae.
ALSO KNOWN AS: Jin Ying Zi, Sugar tangerine, Thorn Chinese olive.
CHINESE USES: Relieves nocturnal emission or leucorrhagia, arrests urinary frequency and enuresis, and astringes the intestine to relieve diarrhea. It is used for nocturnal emission, spermatorrhea, excessive leucorrhagia, frequent urination, abnormal uterine bleeding, protracted diarrhea, and chronic dysentery.
SIDE EFFECTS: It is safe to take orally in moderate amounts. Suggest avoid using during pregnancy and lactation, as there is insufficient reliable information available. May cause fever, thirst, and abdominal discomfort.
C. *Fructus Rubi* (fruit)

*FRUCTUS RUBI* is commonly referred to as Chinese raspberry fruit. It is the dried fruit of the *Rubus chingii* Hu plant. The fruit is collected from July to August when it's not fully ripe and is still green in color. It usually comes from the Zhejiang, Fujian, and Sichuan provinces of China.
SCIENTIFIC NAMES: *Rubus pa/Vifolius*; *Rubus palmatus*; *Rubus chingii Hu*; *Rubus idaeus*, synonym *Rubus strigosus*.
FAMILY: Rosaceae.
ALSO KNOWN AS: Fu Pen Zi, Red Raspberry, Rubus, Palmleaf raspberry fruit.
CHINESE USES: Benefits the kidneys, and arrests seminal discharge and excessive urination. It is used for enuresis, frequent urination, impotence, premature ejaculation, and seminal emission and spermatorrhea in kidney deficiency syndrome.
SIDE EFFECTS: It is safe to take orally in moderate amounts. Suggest avoid using during pregnancy and lactation, as there is insufficient reliable information available. Toxic reports are not known.
D. *Fructus Psoraleae* (fruit)

*FRUCTUS PSORALEAE*, or Malaytea Scurfpea fruit, is the dried fruit of *Psoraleae corylifolia L*. The plant is harvested in autumn when the fruit is ripe. It grows in the Henan and Szechuan provinces.
SCIENTIFIC NAMES: *Psoraleae corylifolia L*
FAMILY: Leguminosae.
ALSO KNOWN AS: Bu Gu Zhi, Scurfy Pea, *Semen Cullinis*, *Cullen corylifoia*, Bauchee seed.
CHINESE USES: Invigorates the kidneys and strengthens the body's yang element. Relieves asthma and cough and promotes smooth respiratory movement. Warms the spleen and kidneys. Stops diarrhea. Kidney deficiency manifested as nocturnal emissions, impotence, enuresis, and frequent urination. Deficiency in kidney and spleen yang that is manifested as aching of the loins and knees coupled with a cold sensation, asthma, and diarrhea. Externally used for vitiligo, alpecia areata, and psoriasis.
SIDE EFFECTS: It is safe to take orally in moderate amounts. It is suggested to avoid using during pregnancy and lactation, as there is insufficient reliable information available.
E. *Radix Morindae Officinalis* (root)

*RADIX MORINDAE OFFICINALIS*, also known as *Morinda*, is the fleshy root of the *Morinda officinalis*. It is harvested in autumn and winter seasons and then dried. The plant grows mainly in the Guangdong, Guangsi and southern Fujian provinces of China.
SCIENTIFIC NAMES: *Morinda officinalis*.
FAMILY: Rubiaceae.
ALSO KNOWN AS: Ba Ji Tian, *Radix Morindae*.
CHINESE USES: Reinforces the kidney-yang, strengthens the tendons and the bones, and relieves rheumatic conditions. Kidney deficiency manifested as impotence, seminal emission, enuresis, frequent urination, and infertility. Rheumatic conditions caused by cold and dampness evils manifested as arthralgia and weakness of limbs.
SIDE EFFECTS: It is safe to take orally in moderate amounts. Suggest avoid using during pregnancy and lactation, as there is insufficient reliable information available.
F. *Fructus Schisandrae Chineusis* (fruit)

*FRUCTUS SCHISANDRAE* is the dried, ripe fruit of *Schisandra chinensis* (Turcz.) Baill. and *S. sphenanthera* Rehd. et Wils. The fruit is harvested between August and October when it turns a purple-red color. The plant grows mainly in the northeastern provinces of China.
SCIENTIFIC NAMES: *Schisandra chinensis* (Turcz.) Baill; and *S. sphenanthera* Rehd. et Wils; other *Schisandra* species.
FAMILY: Schisandraceae. A
ALSO KNOWN AS: Wu Wei Zi, Bei Wu Wei Zi, Chinese Magnoliavine fruit, Five-Flavor-Fruit, *Chinesischer Limonenbaum*, Gomishi, Hoku-Gomishi, Omicha.
CHINESE USES: Replenishes vital energy (qi), promotes fluid secretion, tonifies the kidney, and induces sedation. For insufficient vital enery (qi) and bodily fluid manifested as fatigue, shortness of breath and feeble pulse, palpitation, spontaneous perspiration, night sweats, TABLE 1-continued

HERBS and thirst. Astringes lung-energy and relieves dyspnea and cough. For kidney-deficiency syndrome it is manifested as seminal emission, chronic diarrhea, and leucorrhagia. It is used for heart-deficiency syndrome for palpitation, insomnia, and dreaminess. Powder preparation is used for chronic hepatitis with elevated serum transaminases.
SIDE EFFECTS: It is safe to take orally in moderate amounts. It is suggested avoid using during pregnancy and lactation, as there is insufficient reliable information available.
G. *Fructus Ligustri Lucidi* (fruit)

*FRUCTUS LIGUSTRI LUCIDI*, or Glossy Privet, is the dried ripe fruit of the *Ligustrum lucidum* Ait. The fruit is harvested in December when it turns black. The plant grows in the Zhejiang, Jiangsu, and Hunan provinces of China.
SCIENTIFIC NAMES: *Ligustrum lucidum*.
FAMILY: Oleaceae.
ALSO KNOWN AS: Nu Zhen Zi, Privet, Chinese privet, Dong Qing Zi, To-Nezumimochi, Trueno, White Wastree, *Ligustrum*.
CHINESE USES: It replenishes the liver and kidney, improves eyesight, and darkens the hair. Nourishes the heart and thus has a calming effect. Regulates menstruation. For deficiency of the liver-yin and kidney-yin manifested as dizziness, tinnitus, blurring of vision, weakness of the loin and knees, fever, nocturnal emission, alopecia, and poliosis. Recently, used for seborrheic alopecia, central retinitis, for early cataract treatment. For insufficiency of heart-yin manifested as insomnia, palpitation, and precordial pain. Recently, used for angina pectoris, hyperlipemia, and neurasthenia, especially for those of the yin-deficiency type, also used for treating leukocytopenia and hepatitis.
SIDE EFFECTS: It is safe to take orally in moderate amounts. It is suggested that one avoid using during pregnancy and lactation, as there is insufficient reliable information available. Individuals may experience mild thirst, dizziness, abdominal discomfort, or diarrhea during treatment. Symptoms will cease when the herb is no longer taken.
H. *Semen Cuscutae* (seed)

*SEMEN CUSCUTAE*, or Dodder Seed are the dried seeds of *Cuscuta chinensis Lam*. The ripened fruit is harvested in September and October. The plant grows mainly in the Liaoning, Jilin, Henan, and Hebei provinces of China.
SCIENTIFIC NAMES: *Cuscuta chinensis Lam.; Cuscuta epithymum*.
FAMILY: Convolvulaceae.
ALSO KNOWN AS: Tu Si Zi, Beggarweed; *Cuscutae*, Devil's Guts, Hellweed, Lesser Dodder Scaldweed, Strangle Tare, Dodder of Thyme.
CHINESE USES: Invigorates the kidney, benefits the spleen to relieve diarrhea, nourishes the liver, and improves visual acuity. For kidney-yang or kidney-qi {vital energy) deficiency manifested as impotence, emission, enuresis, frequent urination, sterility, leucorrhagia, soreness of the loin and knees, blurred vision, tinnitus, and deafness. For use in deficiency of the liver and kidney and if individual experiences frequent miscarriages. It nourishes the liver and improves visual acuity: For blurry vision and hypopsia due to liver and kidney disorder. Recently, it was also used for aplastic anemia and chyluria. Externally used for vitiligo.
SIDE EFFECTS: It is safe to take orally in moderate amounts. Suggest avoid using during pregnancy and lactation, as there is insufficient reliable information available.
I. *Radix Astragali* (root)

*RADIX ASTRAGALI*, or Milkvetch Root, is the dried rhizome of the *Astragalus~ membranaceus*. (Fisch.) Bunge var. *mongholicus*. (Bunge) Hsiao or *A. membranaceus* (Fisch.) Bunge.
SCIENTIFIC NAMES: *Astragulus membranaceus; A. membranaceus*. (Fisch.) Bunge var. mongholicus. (Bunge) Hsiao; *A. membranaceus* (Fisch.) Bunge.
FAMILY: Leguminosae.
ALSO KNOWN AS: Huang Qi, Astragalus, Bei Kei, Bei Qi, Buck Qi, Hwang Gi, Mongolian Milk, Qgi, Membranous Milk Vetch.
CHINESE USES: Reinforces vital energy (qi), relieves skin infection, and promotes tissue regeneration. Invigorates the vital energy (qi) and spleen: For spleen-deficiency with poor appetite, loose stool, fatigue, and bleeding. For replenishing the collapse of the middle-jiao energy manifested as prolapse of the rectum, hysteroptosis or gastroptosis. Use on common colds in debilitated patients and superficies-asthenia with profuse sweating. Used to treat unruptured abscess, unhealed carbuncle, skin erosion, unhealed wounds, skin rash diseases, and skin infection of the yin type. Recently, it has also been used for peptic ulcer and atrophic gastritis.
SIDE EFFECTS: It is safe to take orally in moderate amounts. Suggest avoid using during pregnancy and lactation, as there is insufficient reliable information available.

*Herba Epimedii* (xianlingpi) or *Herba epimedium brevicomum Maxim* is the above ground part of *epimedium brevicomum Maxim*. This herb may be used unprepared or stir-baked with sheep fat. Exemplary pharmacological actions include vascular dilation, androgenic activity such as increasing prostate weight in mice, and enhanced lymphocyte-blastogenesis rate. In certain embodiments, a lyophilized powder of an alcohol extract of *Herba epimedium brevicornum Maxim* can be used as a component of a composition. In particular embodiments the herb is used in an approximate range of 25% to 65% weight to weight of the composition preferably 35% to 55%, and more preferably approximately 45% weight to weight of embodied composition(s).

*Radix Morindae Officinalis* (Bajitian) is the fleshy root of *Morinda officinalis*. The root is approximately 1 to 2 cm in length. The cork of the root is a dull grey with annular dehiscence and exposed fine xylem appearing as catena. Cross section of the root shows a thick, fleshy purplish cortex and small round yellow-white xylem that occupies approximately a fourth of the diameter with a slightly dentate margin. The root is sweet and acrid in taste. Exemplary pharmacological actions of the herb are androgenic effects, promotion of the lutenizing action of the hypothalamus-pituitary system, and development of immature granulocytes. In certain embodiments, a lyophilized powder of an alcohol extract of *Radix morindae officinalis* can be used as a component of a composition. In particular embodiments, the herb is used in an approximate range of 1% to 10% weight to weight of the, preferably 2% to 8%, and more preferably approximately 5% weight to weight of embodied composition(s).

*Fructus Rosae Laevigatae* (Jinyingzi) or the fruit of *Rosa Laevigatae* is approximately 2 to 3.5 cm long and 1 to 2 cm in diameter. The skin of the fruit is formed by the calyx tubes and is red-yellow to red-brown with numerous small projections. The inner wall of the fruit is typically yellowish and 1-2 mm thick. The fruit tastes sour. In certain embodiments, a lyophilized aqueous/alcohol extract of the fruit can be used as a component of a composition. Exemplary pharmacological actions include growth inhibition of some viruses, growth inhibition of some bacteria and enhanced digestive function. In particular embodiments, the herb is used in an approximate range of 1% to 20% weight to weight of the composition, preferably 5% to 15%, and more preferably, approximately 10% weight to weight of embodied composition(s).

*Fructus Rubi* (Fupenzi) or the fruit of *Rubus chingii* Hu is an aggregate fruit that is approximately 0.5 to 1.5 cm long and approximately 0.5 to 1.5 cm in diameter at the base. The surface of the fruit is yellow-green to yellow-brown. Exemplary pharmacological action includes estrogen-like effects. In certain embodiments, a lyophilized aqueous/alcohol extract of *Rubus chingii* Hu can be used as a component of a composition. In particular embodiments, the herb is used in an approximate range of 1% to 20% weight to weight of the composition, preferably 5% to 15%, or more preferably 10% weight to weight of embodied compositions.

*Fructus Schisandrac Chinensis* (Wuweizi) or the fruit of *Schisandra chinensis* (Turz.) Baill is approximately 5-8 mm in diameter. The carpodermis is purple-red or dull red with a wrinkled and soft texture. Exemplary pharmacological actions include bacteriostatic action on some bacteria, enhanced lymphocyte-blastogenesis, cardiotonic and sedative actions. In certain embodiment, a lyophilized alcohol extract of *Schisandra chinensis* (Turz.) Baill can be used as a component of a composition. In particular embodiments, the herb is used in an approximate range of 1% to 10% weight to weight of the composition, preferably 2% to 8%, or more preferably approximately 5% weight to weight of embodied compositions.

*Fructus Ligustri Lucidi* (Nuzhenzi) or the fruit of *Ligustrum lucidum* Ait is elliptical, 6 to 8.5 mm long, and 3.5 to 5.5 mm in diameter. The surface of the fruit is typically dark purple with an irregular wrinkled appearance. The pulp of the fruit is generally soft and usually contains a single seed. Exemplary pharmacologic actions have included the prevention of leukocytopenia in mice, enhancement of anoxia tolerance of mice under atmospheric pressure, increases coronary flow in rabbits, relaxes adrenaline-induced vasoconstriction in rabbits, and lowers blood lipid levels. In certain embodiments, a lyophilized aqueous/alcohol extract of *Ligustrum lucidum* Ait can be used as a component of composition. In particular embodiments, the herb is used in an approximate range of 1% to 10% weight to weight of the composition, preferably 2% to 8%, or more preferably approximately 5% weight to weight of an embodied composition(s).

*Semen Cuscutae* (Tusizi) or the seed of *Cuscuta chinensis* Lam is small, round and approximately 1 to 1.5 mm in diameter. The seed surface is typically grey-brown with reticular marks visible under magnification. Exemplary pharmacological actions include promotion of lymphocyte-blastogenesis and cardiotonic actions. In certain embodiments, a lyophilized alcohol extract of *Cuscuta chinensis* Lam can be used as a component of a composition. In particular embodiments, the herb is used in an approximate range of 1% to 10% weight to weight of the composition, preferably 2% to 8%, or more preferably approximately 5% weight to weight of an embodied composition(s).

*Fructus Psoraleae* (Buguzhi) or the fruit of *Psoralea corylifolia* L. is 3 to 5 mm long. The carpodermis is typically dark-brown with fine reticular marks. Exemplary pharmacological actions include dilation of coronary arteries, promotion of macrophage phagocytosis, excitation of intestinal smooth muscle, and relaxation of the uterus in guinea pigs. In certain embodiments, a lyophilized alcohol extract of *Psoralea corylifolia* L can be used as a component of composition. In particular embodiments, the herb is used in an approximate range of 1% to 20% weight to weight of the composition preferably 5% to 15%, and more preferably approximately 10% weight to weight of embodied compositions.

*Radix Astragali* (Huangqi) or the root of *Astragalus membranaceus* [Fisch.] Bge is occasionally branching, 30 to 90 cm long and 1 to 3.5 cm in diameter. Exemplary pharmacological actions include promoting lymphocyte-blastogenesis, promoting healing, cardiotonic actions, and dilating coronary arteries and capillaries. In certain embodiments, a lyophilized aqueous/alcohol extract of *Astragalus membranaceus* [Fisch.] Bge can be used as a component of a composition. In particular embodiments, the herb is used in an approximate range of 1% to 10% weight to weight of the composition, preferably 2% to 8%, and more preferably approximately 5% weight to weight of embodied compositions.

In particular embodiments, components may be provided in dried or lyophilized form. Alternative embodiments may use macerated, ground, chopped, cooked, extracted, and other forms of the herb as components of embodied compositions. The compositions are preferably provided in an ingestible form, such as, a powder, capsule or tablet form.

Extraction

In certain embodiments, herb or plant material may be extracted with alcohol. Preferably, alcohol extraction is performed by using 60% to 80% alcohol at a temperature in the range of 70° to 100° C. for 1 to 3 hours. The extraction procedure may be repeated several times, preferably three times. The extract is then condensed and dried to a powder.

In other embodiments, certain herb or plant material may be extracted with water to produce an aqueous extract. Preferably, an aqueous extraction is created using water, preferably purified water, at temperature of 70° to 100° C. for 1 to 3 hours. The extraction procedure may be repeated several times, preferably three times. The extract may then be condensed and treated with alcohol, as described for alcohol extraction to produce an aqueous/alcohol extract. The extract is then condensed and dried to a powder.

Table II presents a list of nine herbs and identifies (where applicable) an active ingredient for each herb.

TABLE II

Each herb and an identified active ingredient

| | Name of 9 Herbs | Active Ingredients |
|---|---|---|
| 1. | Herba Epimedii (stem and leaves) | icariin |
| 2. | Fructus Rosae Laevigatae (fruit) | ursolic acid |
| 3. | Fructus Rubi (fruit) | ellagic acid |
| 4. | Fructus Psoraleae (fruit) | psoralen |
| 5. | Radix Morindae Officiualis (root) | |
| 6. | Fructus Schisandrae Chinensis (fruit) | deoxyschizandrin |
| 7. | Fructus Ligustri Lucidi (fruit) | oleanolic acid |
| 8. | Semen Cuscutae (seed) | quercetin |
| 9. | Radix Astragali (root) | aslvagaloside |

Table III presents a list of nine herbs and identifies measurement technique for identifying an active ingredient.

TABLE III

| | Name of 9 herbs | Active ingredients Or measurable markers | Concentration of active ingredients in each extract | Concentration of active ingredients in Equiguard (Batch#SH020401) | Method of measurements |
|---|---|---|---|---|---|
| 1. | Herba Epimedii | icariin. | 2.8% (SH001204) 2.9% (SH020305) | 1.6% | HPLC |
| 2. | Fructus Rosae Laevigatae | Glucose $C_6H_{12}O_6$ OR ursolic acid | 90.2% glucose (SH020303) | | UV method/ spectrophotometric |
| 3. | Fructus Rubi | ellagic acid. | | Not tested | No method |
| 4. | Fructus Psoraleae | Psoralen | 1.6% (SH001202) 2.5% (SH020310) | 0.3% | HPLC |
| 5. | Radix Morindae Officinalis | | | Not tested | No method |
| 6. | Fructus Schisandrae Chinensis | Deoxyschizandrin | 0.4% (SH020306) | 0.06% | HPLC |
| 7. | Fructus Ligustri Lucidi | oleanolic acid | 0.034% (SH020302) | 0.013% | TLC |
| 8. | Semen Cuscutae | Quercetin | 0.01% (SH020309) | Not able to be detected | HPLC |
| 9. | Radix Astragali | Astragaloside | 0.365% (SH020304) | Not able to be detected | TLC |

Herba Epimedii

Active Ingredient: Icariin

Chemical Name: 4H-1-Benzopyran-4-one, 3-[(6-deoxy-α-L-mannopyranosyl)oxy]-7-(β-D-glucopyranosyloxy)-5-hydroxy-2-(4-methoxyphenyl)-8-(3-methy-2-butenyl)-

Chemical Structure:

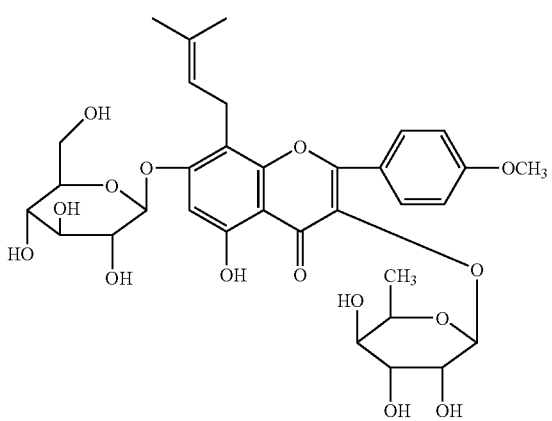

Molecular Formula; Molecular Weight: $C_{33}H_{40}O_{15}$; 676.65

Radix Astragali

Active Ingredient: Astragaloside IV

Chemical Name: 20,24-Epoxycycloartane-3,6,16,25-tetrol 3-O-β-$_D$-Xylopyranoside, 6-O-β-$_D$-glucopyranoside Chemical Structure:

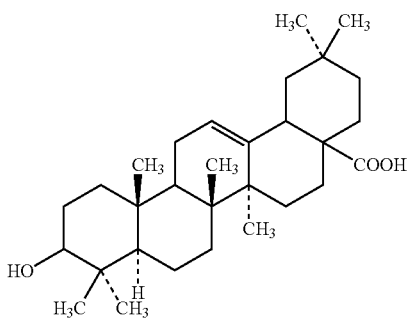

Molecular Formula; Molecular Weight: $C_{41}H_{68}O_{14}$; 784.98

Fructus Ligustri Lusidi

Active Ingredient: Oleanolic Acid

Chemical Name: Olean-12-en-28-oic acid, 3-hydroxy-, (3β)-

Chemical Structure:

Molecular Formula; Molecular Weight: $C_{30}H_{48}O_3$; 456.71

Fructus Schisandrae Chinensis

Active Ingredient: Schisandrin

Chemical Name: Dibenzo [a, c] cycloocten-6-ol, 5,6,7,8-tetrahydro-1,2,3,10,11,12-hexamethoxy-6,7-dimethyl-, Stereoisomer Chemical Structure:

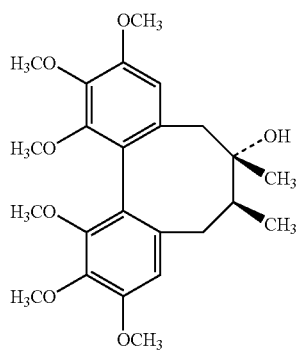

Molecular Formula; Molecular Weight: $C_{24}H_{32}O_7$; 432.50

Semen Cuscutae

Active Ingredient: Quercetin

Chemical Name: 4H-1-Benzopyran-4-one, 2-(3,4-dihydroxyphenyl)-3,5,7-trihydroxy-

Chemical Structure:

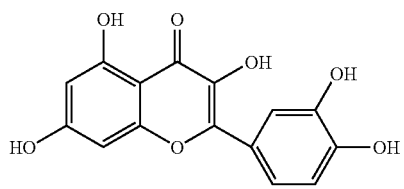

Molecular Formula; Molecular Weight: $C_{15}H_{10}O_7$; 302.23

Fructus Psoraleae

Active Ingredient: Psoralen

Chemical Name: 7H-Furo[3,2-g][1]benzopyran-7-one

Chemical Structure:

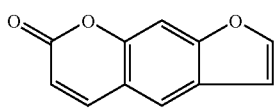

Molecular Formula; Molecular Weight $C_{11}H_6O_3$; 186.16

Composition

Combinations of the ingredients described can improve the overall benefit and/or effect of each of the ingredients individually. For example, with respect to kidney health, the 9-herb composition has synergistic effects. Instead of simply treating one ailment such as an infection, the 9-herb composition can act as an antibiotic followed by balancing and stabilizing the kidney and then boosting the immune response to battle subsequent ailments. The components are chosen and combined according to their biological activities. Each component typically has multiple pharmacological and medicinal actions, examples of which are listed herein.

In one embodiment, extracts of *Herba Epimedii, Fructus Rosae Laevigatae, Fructus Rubi, Fructus Psoraleae, Radix Morindae Officinalis, Fructus Schisandrac Chinesis, Fructus Lugustri Lucidi, Semen Cuscutae*, and *Radix Astragali* may be mixed in a 9:2:2:2:1:1:1:1:1 ratio and made into capsule form (the 9-herb composition). In a 350 mg capsule, for example, the amount of an extract of Herba Epimedii is 157.5 mg. In certain embodiments, the composition may contain at least 3 mg of Icariin. In another embodiment, the components, in the same order, may be mixed in a ratio 35:15:15:10:5:5:5:5:5.

Administration

In certain embodiments, aqueous, alcohol, and aqueous/alcohol extracts of the above components may be used. In particular embodiments, a lyophilized powder form of the components can be used. Aqueous/alcohol extraction is a sequential extraction in which the first extraction is an aqueous extraction and the aqueous extract is extracted using alcohol extraction techniques. The components may be mixed and the composition rendered into an administerable form.

In particular embodiments, compositions will be administered orally as dietary supplements or as a combination therapy. Any suitable route of administration may be employed for providing the patient with an effective dosage of the composition. Oral administration is preferred. Alternative routes of administration include but are not limited to oral, rectal, parenteral, intravenous, topical, transdermal, subcutaneous, and intramuscular.

In certain embodiments, oral dosage forms are preferred. In particular embodiments, the dosage is in the form of a capsule. Dosage forms include, but are not limited to tablets, troches, dispersions, suspensions, solutions, capsules, pill, patches, and suppositories. In specific embodiments, the formulation of the composition may be prepared with binders and fillers.

A suitable dosage of a composition, such as the 9-herb composition include, but are not limited to, 100 to 2500 mg per day for kidney health including prophylatic kidney disorder health and sexual satisfaction. One specific embodiment of a dose of a 350 mg capsule of the 9-herb composition is three capsules twice daily for kidney health. In certain embodiments for prophylaxis of prostate cancer or prostate disorders in an individual in need thereof, the dosage may be in the approximate range of 500 mg per day to 3500 mg, preferably 750 mg to 2100 mg per day. In certain embodiments, the composition may be administered one or more times within a 24-hour period preferably twice daily (e.g., 350 mg capsule, three or more capsules twice daily). In preferred embodiments, the composition can be administered in the morning, afternoon and evening. In other embodiments, the composition may be administered in the morning and evening. In alternate embodiments, the composition may be administered once daily.

Prostate Disorders

In men, the prostate gland is the source of several common disorders including prostatitis and benign prostatic hypertrophy (BPH), wherein the prostrate gland becomes inflamed or enlarged. Prostatitis is defined as an inflammation or infection of the prostate gland. While prostatitis may be acute, associated with systemic findings of fever, chills and rigors, most cases of prostatitis are chronic and tend to be incurable with relatively frequent recurrences despite optimal standard therapy. Chronic prostatitis (inflammation or infection of the prostate) is common to all adult men. It is associated with virtually all cases of prostate cancer and is present in every prostate biopsy regardless of other findings.

The most common symptom of chronic prostatitis is pelvic pain, followed by various voiding symptoms, impotence, and infertility. Pain from prostatitis is usually located in the groin, testicles, and penis, just above the rectum or in the suprapubic area over the bladder. Pain is frequently associated with ejaculation. Typical voiding symptoms produced by prostatitis include getting up several times at night to void (nocturia), frequency and urgency of urination, incomplete voiding, decreased force of the urinary stream, intermittency of the stream and a need to push or strain to void. Impotence or erection difficulties and male infertility are also associated with prostatitis.

BPH occurs naturally in most males over 50 years of age. At this age, the male body begins to transform testosterone (male sex hormone) into dihydroxytestosterone (DHT) at higher levels within the prostate. This is primarily due to the higher levels of the enzyme 5-alpha reductase, which causes the conversion of testosterone to DHT. DHT has an increased affinity for hormone receptors in prostate cells, which ultimately results in prostate enlargement. It is usually benign, therefore, in some cases there is no need for surgery. However, enlargement of the prostate gland can cause many uncomfortable and annoying symptoms. Worsening symptoms may require prostate surgery.

In Chinese medicine, prostate cancer is closely associated with kidney qi deficiency. Prostate cancer occurs frequently in elderly men and this occurrence rate increases with age. During aging, many factors can lead to urinary tract blockage in men. These factors include weaken in kidney qi, decline in vital portal fire, deterioration in qi transformation in urinary bladder or damage of nephron and retainment of blood and sperm due to frequent sexual activity. In an observation on 235 cases of prostate cancer in 18 hospitals in Shanghai, 39% patients experienced difficulties in urination, 15% had urine dribbling, 11.1% found blood in urine (haematuria), 74% had frequent urination. After treated with the 9-herb composition, patients showed improvement in symptoms, especially in the frequency of urination. The formula of the 9-herb composition has two main working principles. The first principle is aimed at correcting the source of disease while the second principle is to alleviate the symptoms associated with the disease. In the first working principle, *Herba Epimedii, Semen Cuscutae, Radix Morindae Officinalis* and *Fructus Psoraleae* are used primarily to tonify kidney yang while *Fructus Ligustri Lucidi* is used secondarily to reinforce kidney yin. All ingredients in the 9-herb composition work together to balance the yin and the yang in the body. The second principle is to retain and promote urination simultaneously. *Fructus Rubi, Fructus Rosae Laevigatae* and *Fructus Schisandrae* are used principally to vitalize kidney and to retain fluid while *Radix Astragali* is used supplementary to nourish qi and promote fluid flow. Consequently, urination will become smooth and thus less frequent. In general, the 9-herb composition can alleviate the symptoms associated with prostate cancer and therefore has certain therapeutic effects on prostate cancer.

In western medicine, prostate cancer is associated with sex hormone disorder and immune function deterioration. Male (androgen) and female (estrogen) hormones have promoting and inhibiting effects on prostate cancer cell growth, respectively. Other than surgery, the major treatment options for prostate cancer are hormonal therapy (like estrogen or anti-androgen therapy treatment) and immune therapy. The efficacy of the 9-herb composition on prostate cancer from a western medicine point-of-view was reviewed, in terms of the 9-herb composition sex hormone like effects, immune modulatory effect as well as anti-cancer effects. Pharmacological studies showed *Fructus Psoraleae, Semen Cuscutae, Radix Morindae Officinalis* and *Fructus Rubi* possess estrogen-like effects while *Radix Astragali* showed estrogen-like promoting effect. In addition, *Fructus Ligustri Lucidi* showed modulatory effects on male and female hormones. In animal studies, male mice treated with *Herba Epimedii* showed decline in sex function while the weight of ovaries and uterus of female mice increased. In addition, male chickens treated with *Fructus Schisandrae* showed decline in sex function. With respect to the 9-herb composition's effect on immune system, several ingredients, *Herba Epimedii, Semen Cuscutae, Radix Morindae Officinalis, Fructus Ligustri Lucidi* and *Radix Astragali*, were recorded to possess immune promoting property. In terms of the 9-herb composition effect on cancer growth, each of *Fructus Psoraleae, Fructus Ligustri Lucidi, Semen Cuscutae, Radix Astragali* and *Fructus Schisandrae* showed anti-cancer effects.

The 9-herb composition is made up of 9 herbs: *Herba epimedium brevicornum* Maxim (stem and leaves), *Radix morindae officinalis* (root), *Fructus rosa laevigatae michx* (fruit), *Rubus chingii* Hu (fruit), *Schisandra chinensis* (Turz.) Baill (fruit), *Ligustrum lucidum* Ait (fruit), *Cuscuta chinensis* Lam (seed), *Psoralea corylifolia* L. (fruit), and *Astragalus membranaceus* [Fisch.] Bge (root). The in vitro data herein presented are consistent with the interpretation that this unique formulation and active ingredients contained therein potentially are efficacious in preventing or treating androgen-responsive and androgen-refractory prostate carcinoma.

General Design. In vitro studies have utilized the androgen-dependent (AD) LNCaP and androgen-independent (HRPC) DU145, PC-3 and JCA-1 cells, to compare and contrast regulation of proteins that respond to extracts of the 9-herb composition.

The use of tissue culture stems from a historical consideration where established cell lines derived from patients carrying diseases with putative genetic aberrations have provided an easily accessible tool and powerful paradigm for elucidating the diseases in question. Research innovations that dated back more than five decades ago have been routinely applied to the establishment and maintenance of permanent cultures from patients; these in vitro models have shown to be invaluable for studying conditions and factors that control the expression of the protein products derived from the aberrant genes, and that presumably is causally related to the disease itself.

In the area of tumor biology, the importance of a malignant cell in an individual diagnosed with cancer is well established, as evidenced by the fact that, when injected into an appropriate host, a single malignant cell alone suffices to give rise to a tumor. For the four cell lines used in these studies, the LNCaP cells, in addition to being androgen-responsive, are also the only established prostate cancer cell lines that retain the ability to synthesize and secrete prostate specific antigen, PSA, which is best known to the public as a marker for prostate carcinoma. Of the three androgen-independent cell lines, PC-3 and DU145 were both derived from metastatic sites, respectively, the bone and the brain, of prostate cancer patients, after subjects had received hormonal therapy. In contrast, the JCA-1, a recently established cell line, has the distinction of being isolated from a primary tumor site of a patient prior to any therapies.

Some of the molecular features characterizing each of these cell lines are presented in Table IV.

TABLE IV

Molecular Features of Established Prostate Cancer Cell Lines

| Cell Line | Source | Androgen dependence | Status |  |  |  |
|---|---|---|---|---|---|---|
|  |  |  | AR/PSA | Rb | p53 | Bcl-2 |
| LNCaP | Metastasis to lymph node | Yes | ++++ | ++ | Wild type | + |
| DU145 | Metastasis to brain | No | Deficient | Truncated | Mutant | ++ |
| PC-3 | Metastasis to bone | No | Deficient | ++ | Null | ++ |
| JCA-1 | Primary | No | Deficient | ++ | Mutant | ++ |

Administration of bioactive agents, to affect cellular proliferation, restore apoptosis, and regulate prostate specific gene expression, while exerting minimal, subclinical toxicity, in target cells is desired. This approach is not predicated with the known information in the pathway sequence leading to development of a particular form of malignancy. The importance of the individual cell in cancer is clear, since a single cancer cell injected into an appropriate host is sufficient to give rise to a tumor. Therefore, many studies have been performed with isolated normal and tumor cells in culture. Historically, cultured cells have also been considered as a powerful easily accessible tool for studying diseases with a putative genetic aberration. Permanent cell cultures from patients can be established in vitro; and serve as model systems for studying conditions and factors that control the expression of the protein products derived from the aberrant genes.

Several cell lines are available for investigating prostate cancer. The LNCaP cells are androgen-responsive and retain the ability to synthesize and secrete prostate specific antigen (PSA), considered to be a critical biomarker for prostate carcinoma. Other commonly used cell lines include PC-3 and DU-145. These three cell lines were derived from metastatic sites, respectively, lymph nodes, bone and brain of prostate cancer patients, after the subjects received hormone therapy. In addition to these three cell lines, a relatively new established cell line, JCA-1, was described. The uniqueness of JCA-1 is that it is derived from a primary tumor site without prior exposure to hormones.

Effect of the 9-herb composition on expression of prostate-specific genes namely PSA. Prostate specific antigen (PSA) is a 34-kDa tissue-specific glycoprotein with; kallikrein-like serine protease activity. It is produced almost exclusively in epithelial cells lining the skin and ducts of the prostate gland. PSA is expressed in normal, benign prostate hyperplasia (BPH), and primary/metastatic prostate tissues. Because PSA levels are elevated in the sera of BPH and prostate cancer patients, previous studies have mostly emphasized its use as a serum marker for diagnosis of patients with prostatic carcinoma, and for monitoring their responses to different forms of therapy. In recent years, however, a number of novel activities with potential important biological implications have been described for PSA. These include its ability to serve as mitogens, involvement in processing of various growth modulators, and acting as an anti-angiogenic agent. PSA is correlated with the clinical staging of prostatic cancer. Serum PSA measures the substance emitted both by the normal prostate gland and by cancerous tissue in the prostate gland. With normal prostate gland, PSA reads between 0 to 4. Elevated PSA (higher than 5) indicates a sign of prostate carcinoma, benign prostate, hyperplasia or prostatitis. The higher the PSA reading, the larger the volume of the cancer.

There was a decrease in PSA present in the media of LNCaP cells cultured for 1-3 days with the addition of ethanolic extracts of the 9-herb composition. Such a decrease probably reflected a reduction in expression of intracellular androgen receptor (AR) as well as PSA.

Effect of the 9-herb composition on G1/S regulatory protein molecules and expression of NFκB. To probe further into the mechanism responsible for the partial cell cycle checkpoint arrest seen in the 9-herb composition extract treated LNCaP cells, western blot analysis was performed. A pronounced decrease in expression of Rb (Retinoblastoma gene) was observed in treated cells, as was the expression of cdc2 (cyclin-dependent kinase). In addition, a precipitous drop in PCNA (proliferating cell nuclear antigen) expression was also noted. Thus, it would appear that the restricted cell cycle progression seen in 9-herb composition treated LNCaP cells is due to a reduced expression of key regulatory protein molecules.

The nature of apoptosis seen in treated cells was also investigated. Results show that treatment with the 9-herb composition reduced the expression of NFκB. Since this molecule is intimately involved in cell survival, its reduced expression could account for the induction of apoptosis observed in the 9-herb composition treated LNCAP cells.

Studies with DU-145 cells. Dissemination of prostate tumor cells often ends in the bone. Accordingly, The effects of 70% ethanolic extracts of the 9-herb composition on growth of DU-145 cells was investigated, which represents prostate cancer cells that metastasize to the bone. Proliferation of these cells was significantly inhibited by the addition of varying concentrations of ethanolic extracts of the 9-herb composition. As little as 1 µl/mL of extract (in media) was sufficient to cause a 25% reduction in cell growth after cells were cultured in the presence of such extract for 3 days. Increasing the concentration of the ethanolic extract resulted in approximately 85% reduction in cell proliferation (3 µl/mL extract). 1 µl/mL of extract is about 73 µg of the 9-herb composition per microliter.

After exposure to the 9-herb composition, the growth suppressive properties were further assessed by analyzing contact-inhibition effects on tumor cells (by colony formation assay). The clonogenicity of DU-145 cells is extremely sensitive to addition of ethanolic extracts of the 9-herb composition, with as little as 1 μl/mL completely abolishing focus forming ability of DU-145 cells.

As with the LNCaP cells, flow cytometry was employed to measure cell cycle distribution. In these cells, however, no G1 arrest was observed, nor was apoptosis induced in these cells. Thus, it seems highly possible that multiple bioactive ingredients are present in the 9-herb composition. Because prostate cancer cells are known to be heterogeneous, the diverse array of bioactive ingredients present in the 9-herb composition supports their potential in the treatment of CaP.

Studies with JCA-1 cells. To obtain information on whether the 9-herb composition exerts a comparable effect on metastasized and non-metastasized, prostate tumors, its effect on growth of JCA-1 cells were studied. JCA-1 cells were established from a primary prostatic site prior to administration of hormonal ablation therapy and may best resemble prostate cancer in situ. Accordingly, the effects of 70% ethanolic extracts of the 9-herb composition on the growth of JCA-1 cells was investigated. Proliferation of these cells WAS significantly inhibited by the addition of varying concentrations of ethanolic extracts of the 9-herb composition. As little as 1 μl/ml of extract was sufficient to cause a 45% reduction in cell growth after cells were cultured in the presence of such extract for 3 days. Increasing the concentration of the ethanolic extract resulted in a much more significant reduction in cell proliferation. This strongly inhibitory property of the 9-herb composition was confirmed using the colony formation assay. The clonogenicity of JCA-1 cells is extremely sensitive to addition of ethanolic extracts of the 9-herb composition, with as little as 1 μl/ml of media completely abolishing the focus forming ability of JCA-1 cells.

In flow cytometric analysis, results obtained with the 9-herb composition treatment of the JCA-1 cells demonstrate that the primary effect, unlike that of LNCaP and DU-145 cells, is an arrest of cell cycle progression in G2/M phase.

Studies with hormone-independent PC-3 cells. The effects of 70% ethanolic extracts of the 9-herb composition were investigated on growth of PC-3 cells. Proliferation of these cells was significantly inhibited by the addition of varying concentrations of ethanolic extracts. As little as 1 μl/ml of extract was sufficient to cause a 70% reduction in cell growth after cells were cultured in the presence of such extract for 3 days. Increasing the concentration of the ethanolic extract resulted in a greater than 95% reduction in cell proliferation. Furthermore, the ability of PC-3 cells to form colonies was completely abolished by as little as 1 μl/ml of the 9-herb composition.

Cell cycle analysis of the 9-herb composition treated PC-3 cells revealed mixed responses. Significant reduction in G1 phase cells was observed, as well as an increase in G2/M. In addition, a small percentage of cells were also shown to undergo apoptosis.

In conclusion, although no one in vitro test is absolutely diagnostic of the ability of cells to form a tumor after implantation into a suitable animal such as an athymic mice, in part due to the fact that conditions in vivo differ sufficiently from those in culture, the combined weight of the evidence is consistent with an anti-prostatic effect by the 9-herb composition.

While not wishing to be bound by theory, the following rationale is offered for the effect of the composition (including the 9-herb composition) on inhibiting or treating prostate cancer. The composition down regulates the receptor of testosterone (androgen receptor). Testosterone needs its receptor to work in the body. Therefore, the composition inhibits the normal function of testosterone. In addition, certain components of the 9-herb composition (i.e., *Herba Epimedii, Fructus Rubi, Fructus Psoralae, Semen Cuscutae*, and *Radix Morindae Officinalis*) effect the sex hormones, suggesting the combination of these herbs (including the 9-herb composition) may work by either stimulating the hypothalamus and pituitary to release leutinizing hormone (LH) and/or increasing the amount of receptors and binding affinity of LH receptors for the production of testosterone or estrogen. The composition may work similar to gonadotropin releasing hormone (GnRH) agonists in the treatment of prostate cancer. By using the composition in conjunction with known GnRH agonists, the dosage may be able to be decreased therefore limiting the testosterone surge and side effects associated with these drugs. A combination of the composition and a GnRH agonist may also shorten the time to down regulate the production of GnRH and shut off testosterone production, which is correlated to the development of prostate cancer.

Another rationale for the effect of the composition on inhibiting or treating prostate cancer is that the composition may also work directly on prostate cancer cells to stop cell proliferation and cause apoptosis. Three herbs have also demonstrated anticancer effects (*Fructus Psoraleae, Semen Cuscutae* and *Fructus Ligustri Lucidi*).

A further rationale is that the composition may also provide some immunomodulatory effects thereby helping immune system to effectively help fight prostate cancer. Herbs demonstrating these effects are *Herba Epimedii, Fructus Rubi, Fructus Psoraleae, Radix Morindae Officinalis, Fructus Schissandrae, Fructus Ligustri Lucidi*, and *Radix Astragali*.

Many herbs possess the function of dual modulation. This means that combination of herbs or the herbs themselves can have the ability to produce a good and bad effect. Sometimes this is predicated on the dosage or the condition of the patient. It is entirely possible that the composition (e.g., the 9-herb composition) may be beneficial for prostate cancer and down regulate testosterone production or work on the prostate cancer cells directly and at the same time be able to treat reproductive problems such as impotence in which testosterone production may need to be stimulated. This means that the 9-herb composition most likely contains bioactive, counter active and balancing properties allowing it to be used for indications that may seem contradictory.

EXAMPLES

The following examples are included to demonstrate preferred embodiments. It should be appreciated by those of skill in the art that the techniques disclosed in the examples which follow represent techniques discovered to function well, and thus can be considered to constitute preferred modes for its practice. However, those of skill in the art should, in light of the disclosure, appreciate that many changes can be made in the specific embodiments which are disclosed and still obtain a like or similar result without departing from the spirit and scope of the embodiments.

In the following non-limiting examples, a representative composition ("the 9-herb composition") of 45% (w/w) *Herba Epimedii*, 10% (w/w) *Fructus Rosae Laevigatae*, 10% (w/w) *Fructus Rubi*, 10% (w/w) *Fructus Psoraleae*, 5% (w/w) *Radix Morindae Officinalis*, 5% (w/w) *Fructus Schisandrac Chinensis*, 5% (w/w) *Fructus Ligustri Lucidi*, 5% (w/w) *Semen Cuscutae*, and 5% (w/w) *Radix Astragali* was used to study the effects of a composition on prostate cell lines.

Unless specified, in Examples 1-18, the 9-herb composition was dissolved into a liquid form in a 70 percent ethanol solution.

The 9-herb composition extraction may be standardized based on its biological activities, i.e., suppression of cancer growth and reduction of PSA. These two parameters were used to develop a standard extraction method, involving systematic increases in the amount of ethanol, from 0-100% in increments of 10%, and a fixed amount of the 9-herb composition. Biological activities of different ethanol extracts were compared. Using this escalating ethanol formula the 9-herb composition was tested. Empirically it was found that the 70% ethanol gave the most consistent results. Briefly, a single capsule of a given lot of the 9-herb composition was suspended in 1 ml of 70% ethanol in 2.0 ml Eppendorf tube. The suspension was shaken at 150 rpm at room temperature for 1 h. Clear extract was obtained by centrifugation and filtration of the suspension. To assay its biological activity, appropriately diluted 9-herb composition ethanol extracts were incubated with prostate cancer cells; control cultures were treated with equivalent volumes of the vehicle, 70% ethanol.

"Quality assurance" of the 9-herb composition, indicative of chemical identity and biological efficacy between lots, was monitored by assays that demonstrate preservation of an acceptable chemical/biological fingerprint. High-pressure liquid chromatography (HPLC) analysis was used to validate the chemical profile, while the ability to elicit defined changes in cell growth/viability and PSA levels in LNCaP cells constitute the biological assay. Biological assay consisted of monitoring inhibition of cell growth, and calculating the amount of the 9-herb composition ethanol extract needed to reduce cell viability by 50% and 90% ($IC_{50}$ and $IC_{90}$), respectively, using androgen-dependent LNCaP and androgen-independent prostate cancer cell lines (DU145, JCA-1 and PC-3).

Example 1

Figure 1:
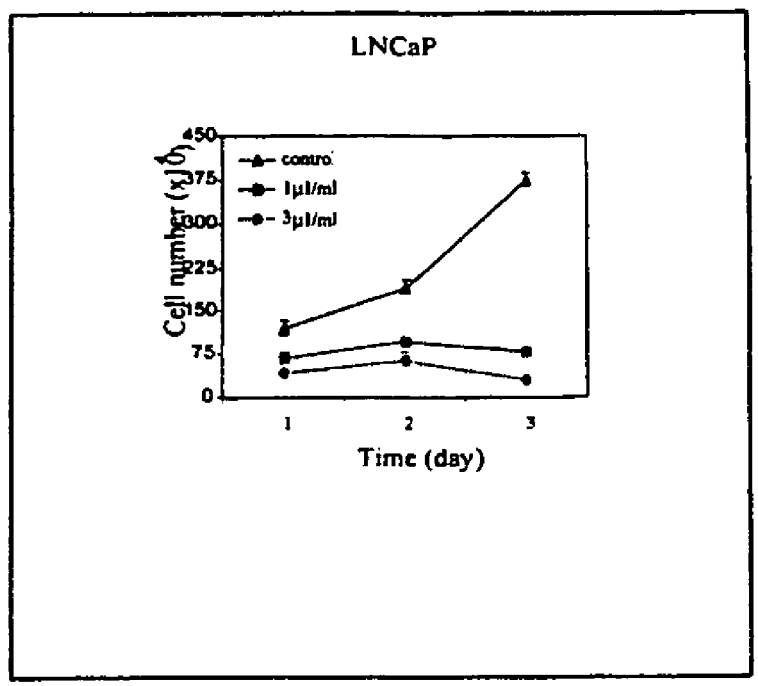
FIG. 1 illustrates the inhibition of LNCaP cell proliferation by embodiments of the composition.

LNCaP Studies. Effects of ethanol extracts of the 9-herb composition on proliferation of androgen-dependent LNCaP cells. FIG. 1 illustrates the inhibition of LNCaP cell proliferation by the addition of varying concentrations of the representative composition. A concentration of 1 μl/mL of extract was sufficient to cause a 30% reduction in cell growth after cells were cultured in the presence of such extract for three days. Increasing the concentration of the extract resulted in a significant reduction in cell proliferation. Addition of ethanol extracts of the 9-herb composition resulted in a dose- and time-dependent reduction in cell growth; whereas control cells proliferated effectively following a slight lag on day 1, cells treated with the 9-herb composition showed little growth. Cells treated with the higher dose of the 9-herb composition had less cells on day 3 compared to day 1. These results suggest that the 9-herb composition elicited both cytostatic (low dose, solid square) and cytotoxic (high dose, solid circle) cellular responses.

Example 2

Figure 2:
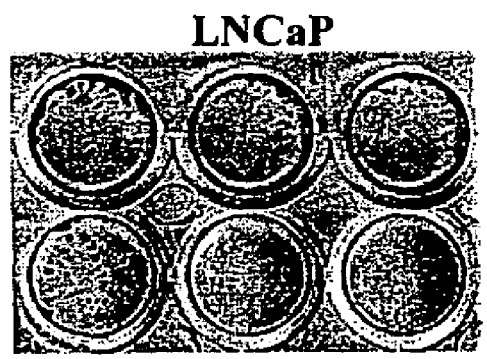
FIG. 2 illustrates the clonogenicity of LNCaP cells to embodiments of the composition.

Inhibition of LNCaP Cell Colony Formation. To further confirm the growth-suppressive property of the 9-herb composition, other growth characteristics of tumor cells in culture were utilized, namely, cell density, tumor cells are typically unrestricted by contact inhibition and will continue to grow and form foci of clustered cell colonies unlike normal cells. This assay is known as a colony formation assay that can be easily performed by fixing and staining cells followed by a period of time in culture. The number of colonies can be quantitated and compared to control conditions. FIG. 2 shows that the clonogenicity of LNCaP cells is extremely sensitive to the addition of extracts of the 9-herb composition. A concentration of 1 μl/ml significantly inhibited colony formation of LNCaP cells.

Example 3

Figure 3:
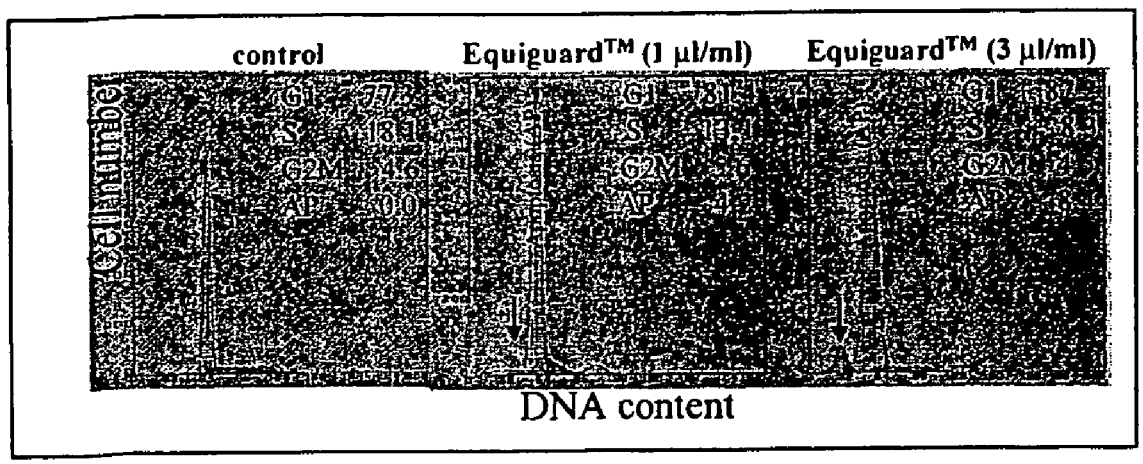
FIG. 3 illustrates the DNA content of LNCaP cells cultured in embodiments of the composition.

Cell Cycle Effects. FIG. 3 shows effects of extracts of the 9-herb composition on cell cycle phase distribution proliferation in androgen-dependent LNCaP cells.

To further test the ability of ethanolic extracts of the 9-herb composition to affect properties of tumor cells in culture, flow cytometry was employed to measure cell cycle distribution. This is an automated technique that quantifies the relative number of cells in G0+G1, S, or G2+M phases of the cell cycle. Cultured cells are suspended as single cells, and stained with a fluorescent DNA dye. The sample of cells than flows past a light source and a detector records the relative DNA content (measured by the amount of fluorescent signal per cell). This graph is a reflection of the relative percents of cells in each phase after the various treatments. FIG. 3 shows the DNA content of LNCaP cells cultured in the presence of the 9-herb composition extracts for 72 hours. This reflects the DNA content of the cancer cell at different stages of the cell cycle. Cells in G2 and M phase of the cell cycle were unaffected. In contrast, cells in S phase decreased, concomitant with G1 phase increase. Interestingly, in cells treated with different concentrations of the 9-herb composition, an additional peak, characteristic of cells undergoing apoptosis, or programmed cell death, is present in treated LNCaP cells.

Cultures were exposed to varying concentrations of the 9-herb composition extracts (1 and 3 μl/ml) for 3 days and harvested. Cells were washed once with PBS and stained with 1.0 μg/ml DAPI containing 100 mM NaCl, 2 mM $MgCl_2$ and 0.1% Triton X-100 (Sigma) at pH 6.8. The DNA-specific DAPI fluorescence was excited with UV light and collected with appropriate filters in an ICP-22 (Ortho Diagnostic, Westwood, Mass.) flow cytometer. The data from each treatment was collected and analyzed by MULTICYCLE™ software provided by Phoenix Flow Systems (San Diego, Calif.). Flow cytometric analysis revealed that treatment with the 9-herb composition resulted in a dose-dependent $G_1/S$ arrest and induction of apoptosis in treated cells.

Example 4

Figure 4:
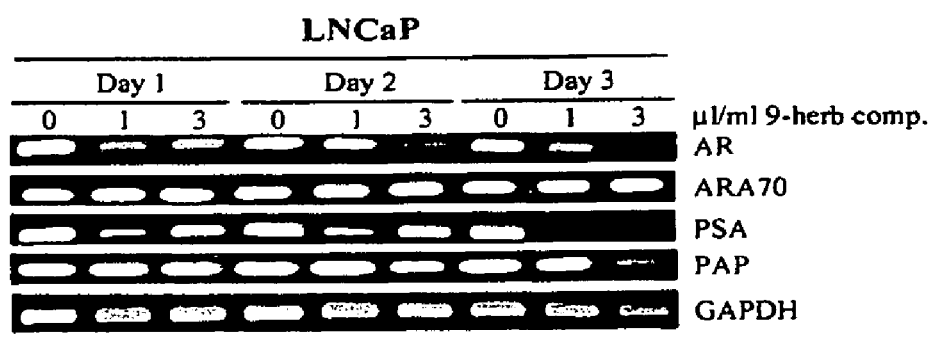
FIG. 4 illustrates PSA levels of LNCaP cells cultured for three days in the presence of embodiments of the composition.

Regulation of PSA expression. Prostate specific antigen (PSA) is a 34-kDa tissue-specific glycoprotein with kallikrein-like serine protease activity. It is produced almost exclusively in epithelial cells lining the acini and ducts of the prostate gland. PSA is expressed in normal, benign prostate hyperplasia (BPH), and primary/metastatic prostate tissues. Because PSA levels are elevated in the sera of BPH and prostate cancer patients, previous studies have mostly emphasized its use as a serum marker for diagnosis of patients with prostatic carcinoma, and for monitoring their responses to different forms of therapy. In recent years, however, a number of novel activities with potential important biological implications have been described for PSA. These include its ability to serve as mitogens, involvement in processing of various growth modulators, and acting as an anti-angiogenic agent. PSA is also reasonably well correlated with the clinical staging of prostatic cancer. Serum PSA is a diagnostic parameter that has been used to monitor the stages of cancer development and the progress of the therapy. Serum PSA measures the substance emitted both by the normal prostate gland and by cancerous tissue in the prostate gland. In a normal prostate gland, PSA is between 0 to 4 units. Elevated PSA (higher than 5) indicates a sign of prostate carcinoma, benign prostate hyperplasia or prostatitis; the higher the PSA reading, the larger the volume of the cancerous growth. FIG. 4 shows the decrease in PSA present in the media of LNCaP cells cultured for three days in the presence of ethanolic extracts of the 9-herb composition.

As already mentioned, the cornerstone in the treatment of AD or AI CaP is androgen deprivation, which results in inhibition of androgen signaling and expression of androgen-responsive genes in CaP cells. Although molecular mechanisms involved in the genesis of HRPC are not fully understood, a wealth of evidence point to participation by structurally changed AR and ensuing signaling pathways. These include 1) growth factor/cytokine mediated signaling events, 2) altered transcriptional control involving AR ligand-independent mechanisms, 3) modified AR.

Changes in RNA expression of a number of genes (AR, ARA70, PSA and PAP) have been analyzed due to the likely importance in the action of the 9-herb composition. Expression of these genes was investigated in control and the 9-herb composition-treated LNCAP cells using RT-PCR and specific primer sets. Results in FIG. 4 demonstrate that expression of AR, PSA show a copious and coordinated decrease even in the presence of the low dose of the 9-herb composition. At the high dose of the 9-herb composition, PSA did not decrease whereas AR did, suggesting that a complex mechanism may be involved in the control of PSA by the AR. By day 3, even the expression of PAP, another marker for prostate cancer, was significantly reduced at the high dose of the 9-herb composition.

Example 5

FIG. 5 shows a scheme depicting the involvement of IL-6 and its upstream/downstream events in the control of PSA expression, cell growth and survival in human prostate cancer cells.

Functions of IL-6 are mediated by two membrane receptor components, a ligand-binding receptor IL-6R and a protein gp130 that serves as signal-transducing molecule for IL-6 and a number of other cellular effectors. Binding of IL-6 to IL-6R facilitates consequent binding of cell-surface attached gp130 and its dimerization. Dimerized gp130 activates JAK family tyrosine kinase, by tyrosine phosphorylation in trans of the JAK kinases, associated with cytoplasmic tail of gp130. The activated JAK kinases, in turn, carry out tyrosine phosphorylation of up to five discrete "docking" sites in the cytoplasmic tail of gp130, which are considered crucial in the subsequent recruitment of STAT-3.

Example 6

FIG. 6 and FIG. 7 show effects of ethanol extracts of the 9-herb composition on expression of IL-6, LIFR, and gp130 in androgen-independent JCA-1 cells.

Changes in expression of IL-6 and related proteins in JCA-1 cells were analyzed. These studies showed that these genes were much less responsive to the 9-herb composition compared to LNCaP cells (FIG. 7). Also, expression of gp130 was not affected in JCA-1 cells, although it was significantly reduced after 3-day treatment with the higher concentration of the 9-herb composition in LNCAP cells (FIG. 6). These data are consistent with the interpretation that the herbal formulation display selectivity in its interaction with target cells. Taking these results as a whole, it would appear that the 9-herb composition is more active in preventing AD→HRPC transition.

Example 7

FIG. 8 and FIG. 9 demonstrate the presence or absence of key regulatory molecules as indicators of cell survival Rb and NFκB (nuclear factor kappa B) after exposure to the 9-herb composition in LNCaP cells. Rb protein was nearly abolished after the herb treatment and NFκB was dramatically reduced. PCNA was also reduced. This data indicates the ability of the herbs to augment key cell survival regulatory molecules and actively modify the survival rate of the LNCaP cells.

Example 8

Du-145 Studies. Prostate tumor cells frequently metastasize to the bone. Accordingly, the effects of 70% ethanolic extracts of the 9-herb composition on the growth of DU-145 cells were investigated. DU-145 cells are representative of prostate cancer cells that have metastasized to the bone. FIG. 10 graphically illustrates that proliferation of these cells was significantly inhibited by the addition of varying concentrations of ethanolic extracts of the representative composition. A concentration of 1 µl/ml of extract was sufficient to cause a 25% reduction in cell growth after cells were cultured in the presence of such extract for three days. Increasing the concentration of the ethanolic extract resulted in about 85% reduction in cell proliferation.

Example 9

Inhibition of DU-145 Cell Colony Formation. The growth-suppressive property of the 9-herb composition was studied further by checking whether escape from contact inhibition characteristic of tumor cells, otherwise referred to as colony formation, are affected by exposure to the 9-herb composition. This assay was performed by fixing and staining the cells followed by a period of time in culture and the number of colonies can be quantitated against the background. FIG. 11 shows that the colony forming ability of DU-145 cells is extremely sensitive to addition of ethanolic extracts of the 9-herb composition, with a concentration of 1 µl/ml completely abolishing the colony forming ability of DU-145 cells.

Example 10

Cell Cycle Analysis of DU-145 Cells. To further study the ability of ethanolic extracts of the 9-herb composition to affect properties of tumor cells, flow cytometry as described above was employed. FIG. 12 shows the DNA content of DU-145 cells (prostate cancer cell line) in the presence of the 9-herb composition extract for 72 hours. The graph reflects the DNA content of the cancer cell at different stages of the cell cycle. In these cells, no G1 arrest was observed, nor was apoptosis induced in these cells. These results suggest the possibility of another mechanism affecting the flow cytometry results compared to the LNCaP cells. Because prostate cancer cells are known to be heterogeneous, the large array of bioactive ingredients present in the 9-herb composition attests to their potential in the treatments of carcinoma of the prostate and other cancers or proliferative diseases.

In conclusion, the evidence is consistent with an anti-proliferative effect of the 9-herb composition.

To test whether the 9-herb composition may also affect androgen-independent prostate cell growth, the studies using JCA-1 cells were repeated.

Example 11

FIG. 13 reflects the effects of ethanol extracts of the 9-herb composition on proliferation of androgen-independent JCA-1 cells. These cells, as indicated earlier, are established from the primary tumor site of an individual before any therapy was administered; as such, these cells probably best mimick the cellular state of primary prostate tumors. Studies with non-metastasized JCA-1 cells were carried out to obtain information on whether the representative composition exerts an effect on metastasized and non-metastasized, prostate tumor cells. The effect of the representative composition on the growth of JCA-1 cells was studied. JCA-1 cells were established from a primary prostatic site prior to administration of hormonal ablation therapy and may best resemble prostate cancer in situ. Effects of the 9-herb composition on cell cycle phase distribution in JCA-1 cells. As with LNCaP cells, growth of JCA-1 cells was significantly reduced by the 9-herb composition in a dose- and time-dependent manner. Contrary to LNCaP cells, however, which responded to the 9-herb composition by being arrested in the $G_1/S$ phase of the cell cycle, flow cytometry analysis of JCA-1 cells treated with the 9-herb composition showed an inhibition in $G_2/M$ traverse.

Example 12

Inhibition of JCA-1 Colony Formation. To further confirm the growth-suppressive property of the 9-herb composition, the colony formation assay or focus-forming assay described above was utilized. FIG. 14 shows that the colony formation ability of JCA-1 cells is extremely sensitive to addition of ethanolic extracts of the representative composition. A concentration of 1 µl/ml of media completely abolished focus-forming ability of JCA-1 cells.

Example 13

Cell Cycle Analysis of JCA-1 Cells. To further study the ability of ethanolic extracts of the 9-herb composition to affect properties of tumor cells, flow cytometry was employed as described above. FIG. 15 shows a graph of JCA-1 cells in the presence of the 9-herb composition for 72 hours. The graph reflects the DNA content of the cells at different stages of the cell cycle. In flow cytometric analysis, results obtained with JCA-1 cells treated with the 9-herb composition shows that the primary effect, unlike that of the LNCAP and DU-145 cells, is an arrest of the cell cycle progression in G2/M phase.

In conclusion, the evidence is consistent with an anti-proliferative effect of the 9-herb composition. FIG. 15 also shows JCA-1 cells in the absence of the 9-herb composition at 72 hours and no apparent change in the graph was observed.

Example 14

PC-3 Studies. Studies with hormone-independent PC-3 cells were conducted to further study the effects of the representative composition on prostate cancer cells. The effect of 70% ethanolic extracts of the 9-herb composition on the growth of PC-3 cells was studied. FIG. 16 illustrates growth inhibition of PC-3 cells by the addition of varying concentrations of ethanolic extracts of the representative composition. A concentration of 1 µl/ml of extract was sufficient to cause a 70% reduction in cell growth after cells were cultured in the presence of such extract for three days. Increasing the concentration of the ethanolic extract resulted in a greater than 95% reduction in cell proliferation.

Example 15

Inhibition of PC-3 Colony Formation. To further study the growth-suppressive property of the 9-herb composition colony formation or focus forming assay was used as described above. FIG. 17 shows that the clonogenicity of PC-3 cells is extremely sensitive to addition of ethanolic extracts of the representative composition. A concentration of 1 µl/ml completely abolished focus-forming ability of PC-3 cells.

Example 16

Cell Cycle Analysis of PC-3 Cells. To further study the ability of ethanolic extracts of the 9-herb composition to affect properties of tumor cells, flow cytometry was used to measure cell cycle distribution as described above. FIG. 18 shows the DNA content of PC-3 cells in the presence of herbal extract for 72 hours. The analysis reflects the DNA content of the cancer cell at different stages of the cell cycle. Cell cycle analysis of PC-3 cells treated with the representative composition revealed mixed responses. A trend of reduction in G1 was observed, as well as an increase in G2/M suggesting an arrest at the G2/M phase. In addition, a small percentage of cells were also shown to undergo apoptosis.

Example 17

Further investigation of the anti-prostate cancer activities of the 9-herb composition using target-specific array analysis. The target array approach is a panoramic analysis of gene expression based on binding of mRNAs prepared from control and treated cells to an ordered array of cDNA molecules of known sequence immobilized on glass or nylon. In our pilot studies involving the use of SuperArrays (SuperArray, Bethesda Md.), mRNAs are hybridized to a defined matrix on nylon sheets containing hundreds of printed cDNA probes. This method is designed to identify existing genes modulated by the 9-herb composition, which could be applied to the standardization of the 9-herb composition extracts. The low-density (pathway specific) platform was chosen over more complex high-density microarrays for its reproducibility, ease of handling with existing resources, and simpler data interpretation. Limitations of this approach include an inability to discover unidentified genes and lower sensitivity, since this assay is more suitable for detecting genes of high abundance.

To determine the validity and application of this method, a study was performed with samples from 48 hour control and the 9-herb composition treated LNCaP cells using the "Human Cancer Pathway Finder GEArray Q series.". Each gene presented in this array appears as four printed spots. In addition, GAPDH and actin (as positive controls) and negative controls are also included to facilitate data normalization using the software provided by the manufacturer, and to compare results from different experiments.

Total RNA was isolated from control and treated cells using Trizol reagent. Possible DNA contaminations were removed by incubation with DNA-free DNase. Four micrograms of RNA was used as the template for cDNA synthesis. Hybridization of biotinylated cDNA to immobilized gene-specific cDNAs and detection of signals using chemiluminescence were performed according to the manufacturer's protocol, as briefly described in Table V.

TABLE V

Protocol for "Human Cancer Pathway Finder GEArray Q Series"

| Step | Procedure |
|---|---|
| 1 | Prehybridization using sheared salmon sperm DNA containing solution, 2 h, 60° C. |
| 2 | Hybridization with the denatured cDNA probe, continuous agitation at 10 rpm/min, 60° C. |
| 3 | Washing with pre-warmed 2× SSC and 1% SDS, followed by 0.1 SSC and 0.5% SDS |
| 4 | Blocking using GEA blocking solution Q |
| 5 | Incubation of membrane with 1:7500 AP-streptavidin, 10 min, room temperature |
| 6 | Reaction with chemiluminescent substrate, multiple exposures to X-ray films |
| 7 | Data analysis using GEArrayAnalyzer software |

GEArrayAnalyzer software was used for the data analysis.

FIG. 19 shows array analysis of gene expression in 48 hours of a control and the 9-herb composition treated LNCAP cells. Total RNA was isolated from control and treated cells using Trizol reagent, after possible DNA contaminants was removed with DNase. Four µg of RNA was reverse transcribed to biotinylated cDNA, which was hybridized to immobilized gene-specific cDNAs using "Human Cancer PathwayFinder GEArray Q series." The signals were detected by chemiluminescence, as detailed by the manufacturer. The software provided by the manufacturer was used for the data analysis. Comparing the effects of a 48 hour treatment of the 9-herb composition, with untreated LNCaP cells, the 9-herb composition treatment results in increases, decreases, and unchanged gene expression. Composite results of several arrays were combined and presented in Table VI.

TABLE VI

Results of Array Analysis

| Array used | Genes increased by the 9-herb composition | Genes decreased by 9-herb composition |
|---|---|---|
| Human CancerPathway finder | c-fos, p27, c-jun | Akt, bax, bcl-XL, survivin (API4), cyclin D1, E-cadhedrin, cdk4, p16, beta-catenin, integrin-B1, mdm2, MMP-1, NCAM1, IkB-alpha, PDGF-alpha, DNA-PK, MTS-1 |
| Significance of finding | Since p27 is a checkpoint kinase inhibitor, this result supports cell cycle arrest by 9-herb composition. | Down regulation of some of these genes support the finding that Equiguard induces $G_1/S$ checkpoint arrest (by reducing cyclin D1 and cdk4). |

Additional array analysis was performed using the apoptosis platform from Superarrays. These results show that the expression of a number of anti-apoptotic genes is significantly down-regulated by incubation with the 9-herb composition.

Results of these preliminary array analyses support the proposition that the multitude of cell, biochemical, and gene responses elicited by the 9-herb composition can serve as markers for its use as a reference standard for further characterizing the anti-prostate cancer activity of extracts of the 9-herb composition. The same experimental strategy could be extended to address the 9-herb composition extract induced $G_1/S$ arrest. The array analyses are expected to further elucidate the mechanism of action of the 9-herb composition. These data may also provide details on how the PSA gene can be controlled.

Example 18

Further analysis was used for confirmation of results of array analysis using real-time PCR. Emphasis will be given to those genes greatly elevated (>3-5 fold) or suppressed (>60%) by extracts of the 9-herb composition. In FIG. 20, Real-time PCR analysis of gene expression in cultured mammalian cells. Real-time PCR is a highly sensitive assay that allows for the precise quantification of mRNA levels. The principle of the method is based on a fluorogenic probe containing both a reporter and quencher dye. When the probe is not in use, fluorescence of the respective reporter and quencher dye is reciprocally quenched, such that there is negligible signal. During each PCR amplification cycle, the probe becomes annealed to the target sequence, and the reporter dye is cleaved from the probe by the nuclease activity of the Taq polymerase. This generates a sequence-specific fluorescent signal from the quencher dye of the probe, which accumulates as the PCR reaction continues. The result is a proportional increase in the fluorescent signal in real time. This figure illustrates that real-time PCR has been successfully applied in this laboratory to the analysis of cyclooxygenase-2 expression in cultured mammalian cells, upon exposure to a variety of modulating agents.

By comparing data obtained in acute (short term) versus chronic (long term) exposure to the 9-herb composition, it may be possible to have a reasonable estimation of the time required for entry and response in target cells and the duration of the effects this herb elicits. A comparison of gene responses between AD and HRPC cells may also provide information on candidate genes which could be involved in the transition between the latent and advanced stages of prostate cancer. Finally, evaluation of gene responses in normal versus cancerous prostate cells may provide insights on genes which could be involved in the initiation of the prostate cancerous state.

Example 19

Effect of the 9-herb composition on kidney deficiency in rats. To study the effects of the 9-herb composition on polyuria induced by hydrocortisone treatment in rats. Animals were observed for three days before experiments. Animals of similar weight were randomly divided into 5 groups. Except animals in normal group, all animals were orally administered with hydrocortisone (50 mg/kg/day, once per day) for two days. On the third day, animals in groups 3 to 5 were administered with corresponding medications and hydrocortisone. On the tenth day, each animal was fed with water (5 ml/kg) before housing in metabolic cage. After 3 hours, urine samples were collected and urination was expressed as vol/100 g. T-test was used to compare the results between groups. The amounts of urine collected from rats in experimental group were significantly higher than those from normal group (p<0.01), suggesting successful experimental polyuria. Rats administered with all three dosages of the 9-herb composition showed significantly reduction in urine volume (p<0.01). Reduction in urine volume was inversely proportional to the dosage of the 9-herb composition administered. However, animals' urination could not be normalized at all dosages being tested.

TABLE VII

Effects of 9-Herb Composition on hydrocoritisone induced polyuria in rats (x ± s, n = 10)

| Group | Normal | Experimental | 9-herb comp. |
|---|---|---|---|
| — | 6.7 ± 0.3 | 13.7 ± 0.5- | — |
| High dose | — | — | 11.6 ± 0.5-_ |
| Moderate dose | — | — | 8.9 ± 0.2-_ |
| Low dose | — | — | 7.8 ± 0.6-_ |

-p < 0.01 comparing to normal group
_p < 0.01, comparing to experimental group

Example 20

The effects of the 9-herb composition on nephritis (proteinuria) in rats. Animals were observed for three days before experiment. Animals of similar weight were then randomly divided into 5 groups. Except animals in normal group, all animals were intravenously injected with adriamycin (7 mg/kg/time). On the second day, animals were orally administered with corresponding medications and i.v. injected with adriamycin. On the eighth day, all animals were fed with $dH_2O$ (5 ml/kg) before housing in metabolic cage. After 24 hours, urine samples were collected and urination was expressed as vol/100 g. T-test was used to compare results between groups. To measure protein content in urine, 0.5 ml urine samples were centrifuged and the amounts of protein were measured by Single Tungsten method. Protein content was expressed as amount/100 g. T-test was used to compare the results between groups. There is a trend of decrease in urine volume when rats were rendered nephritis, however, no statistical significance was detected (p>0.05). Nephritis rats treated with high dose of the 9-herb composition showed significant increased in urine volume (p<0.01) while those treated with low dose showed significant decreased in urine volume (p<0.01).

TABLE VIII

Effects of 9-Herb Composition on urination in adriamycin induced nephritic rats (x ± s, n = 10)

| Group | NORMAL | Experimental | 9-herb Composition |
|---|---|---|---|
| — | 11.3 ± 1.2 | 10.5 ± 0.6 | — |
| High dose | — | — | 13.7 ± 0.3- |
| Moderate dose | — | — | 10.8 ± 0.8 |
| Low dose | — | — | 8.9 ± 0.8- |

-p < 0.05, -p < 0.01, comparing to normal group.
_p < 0.01, comparing to experimental group.

TABLE IX

Effects of 9-Herb Composition on protein content in adriamycin induced nephritic rats (x ± s, n = 10)

| Group | NORMAL | Experimental | 9-Herb Composition |
|---|---|---|---|
| — | 4.56 ± 0.56 | 5.91 ± 1.54- | — |
| High dose | — | — | 5.10 ± 1.33- |
| Moderate dose | — | — | 5.72 ± 0.57 |
| Low dose | — | — | 2.94 ± 0.76- |

-p < 0.05, -p < 0.01, comparing to normal group.
_p < 0.05, _p < 0.01, comparing to experimental group.

Example 21

The 9-herb composition and Incontinence. 70-year old male diagnosed with having an enlarged prostate suffered from frequent-urination problems including increased daily frequency and reduced volume. He had the urge to urinate every two hours and the amount was only a few drops. His symptoms were attributed to old age. The patient was prescribed PROSCAR™ for his enlarged prostate, but this did not alleviate the urination problem. The patient then began taking six capsules of a 350 mg dose of the 9-herb composition each day (3 tablets in the morning and 3 tablets in the evening). After a period of time on this regimen, his urinary frequency decreased. The man reports that he only goes to the bathroom every four hours instead of every two hours during the day. He is able to urinate what he considers a normal amount of urine in a steady stream as opposed to the dribbling he experienced prior to taking the 9-herb composition. The biggest benefit he experienced, however, is sleeping through the night without having to get up and go to the bathroom. Because he is sleeping better, he has more energy throughout the day.

Example 22

Effects of the 9-herb composition on nocturnal urination in elderly people. The purpose of this study was to study the effects of the 9-herb composition on frequent urination problems as a reflection of kidney deficiency in elderly people. Based on an in-house kidney deficient evaluation chart, 45 subjects (20 male and 25 female) were recruited from Cheng Duo Old Folks Home for this study. The average age was 80.46 years old and the average nocturnal urination frequency was 4 times/night. The subjects were divided into 3 groups: the 9-herb composition, Shuang Nao Shen or placebo. (Shuang Nao Shen is another herbal product thought to treat nocturnal urination frequency.) One week before the study, frequency, quality and specific gravity of urination was evaluated. Then the subjects were treated for three weeks with their designated medication. After treatment the subjects were observed for one week. Urine samples were collected one day before and one day after the treatment and analyzed.

The 9-herb composition group showed significant improvement in nocturnal urination frequency after treatment. Since pathogenesis of kidney deficiency during aging is a long process and many mechanistic functions in elderly people are deteriorating, it takes a long time to restore the kidney function in elderly people. In western medicine, glomerulosclerosis is the major cause of kidney function deterioration. Glomerulosclerosis can lead to 20% to 30% or even 50% reduction in functional glomerulus4. Medication for promoting glomerulus function and restoring or inhibiting the pathogenesis of glomerulosclerosis takes times to have effect. Because of the constraint in time, the duration of the present study was designed to be three weeks. Regardless, the 9-herb composition showed improvement in nocturnal urination frequency (a decrease) to warrant a longer duration study.

Example 23

The effects of the 9-herb composition on sexual satisfaction was studied. The results are presented in Table X below. At the time of the interview all the subjects were still using the 9-herb composition. The average age of the six men interviewed that was 31.8 years with a range in age of 26-37. All were of Chinese decent. Prior to taking the 9-herb composition, the men reported reaching ejaculation during sexual activity an average of 8.3 times per month with a range of (4-10). The average time of a sustained erection was 8.3 minutes with a range of 5-15 minutes. All except one interviewee who did not respond reported having an "okay" sex life with no history of any sex problems.

All six men too the 9-herb composition for a minimum of four months and one person a maximum of nine months. The average length of use was 5.8 months. The dosage each man took ranged from one (350 mg) capsule to three capsules per day (average 2.2 capsules/day). At the time of the interview all men except one reported an increase in the number of sexual activities they engaged in which resulted in ejaculation. The range in number of ejaculations was 8-30 per month with an average of 15.3 ejaculations per month. There was an average 84.3% increase in number of ejaculations per month after taking the 9-herb composition (range 0-400%). The amount of time an erection could be sustained also increased from an average of 6.75 min to 13.5 minutes, which was a 100% improvement. All six men reported an improvement in the quality of their sex life. Five of the six interviewed candidates reported feeling more energetic and four reported having a longer erection as benefits of the 9-herb composition. Side effects perceived by the interviewees included two person reporting feeling increased thirst, two having hot flashes, and two with an increased sex desire.

TABLE X

Effect of a 9-Herb Composition on Sexual Satisfaction

|  | Case 1 | Case 2 | Case 3 | Case 4 | Case 5 | Case 6 | Average |
|---|---|---|---|---|---|---|---|
| Age | 34 | 33 | 26 | 30 | 37 | 30 | 31.8 |
| Ethnicity | Chinese | Chinese | Chinese | Chinese | Chinese | Chinese | Chinese |
| Other medications or treatments | No | Not specify | No | No | No | No | N/A |
| Before taking 9-herb composition | | | | | | | |
| Number of sexual activities with ejaculation per month | 10 | 8 | 10 | 8 | 4-8 | 8 | 8.3 |
| Average length of erection | 5 min | 15 min | 5-6 min | 5 min | 5 min | 5 min | 6.75 min |
| Sex problem (i.e., inability to ejaculate or ejaculating too quickly). | No | No | No | No | No | No | N/A |
| Quality of sex (really good, good, okay, not so good, really bad) | Okay | Okay | Okay | Okay | Okay | Okay | N/A |
| After taking 9-herb composition | | | | | | | |
| Dose taken (# of capsules taken__ times/day) | 1/1 | 3/1 | 3/1 | 2/1 | 2/1 | 2/1 | 2.2/1 |
| Start from__to__. (months) | October 2001 to present (9 mo) | December 2001 to present (7 mo) | February 2002 to present (5 mo) | January 2002 to present (6 mo) | March 2002 to present (4 mo) | March 2002 to present (4 mo) | 5.8 mo |
| Number of sexual activities with ejaculation per month | 15 | 12-15 | 18 | 12 | 20-30 | 8 | 15.3 |
| % increase in # ejaculations | 50% | 50-88% | 80% | 50% | 233-400% | 0% | 84.3% |
| Average length of erection | 10-15 min | 25 min | 10-15 min | 10 min | 5-20 min | 8-10 min | 13.5 min |
| % increase in time of erection | 100-200% | 67% | 82-173% | 100% | 0-300% | 60%-100% | 100% |
| Sex problem (improve or get worse, enter N/A if no sex problem before taking Equiguard ™) [brief description] | N/A | N/A | N/A | N/A | N/A | N/A | N/A |
| Quality of sex (really good, good, okay, not so good, really bad) | Good | Good | Good | Good | Really good | Good | N/A |
| Improvement in quality of sex | Yes | Yes | Yes | Yes | Yes | Yes | N/A |
| After taking 9-herb composition | | | | | | | |
| Benefits experienced after taking | Longer erection | More energetic during wake | Feel more energetic, flasher | Longer erection; more | Longer erection; can have | Longer erection; can have | N/A |

TABLE X-continued

Effect of a 9-Herb Composition on Sexual Satisfaction

| | Case 1 | Case 2 | Case 3 | Case 4 | Case 5 | Case 6 | Average |
|---|---|---|---|---|---|---|---|
| 9-herb composition. Describe. | | up, have better performance in sex life (time), more frequent to have sex. | mind, more difficult to feel tired. | energetic; fresh mind; not so dizzy during wake up | another intercourse within 15-20 min; more energetic; fresh mind; not so dizzy in daily life. | another intercourse within 15-20 min; more energetic; fresh mind; not so dizzy in daily life. | |
| Side effects experienced while taking 9-herb composition. | Always want sex | Very easy to have hot flashes(very hot and heat in the body) | Easy to feel thirsty. | No | More sex desire, feel hot flashes | Easy to feel thirsty; need to drink more water, more sex desire. | N/A |

The regular administration of an embodiment of the composition over time results in improved sexual fitness, i.e., function, desire, and satisfaction (e.g., energy and stamina in males). Embodiments of the composition (e.g., the 9-herb composition) should similarly benefit erectile dysfunction (e.g., impotence). Similar sexual fitness results may be extrapolated to improved sexual fitness in women (e.g., energy and clitoral stimulation in females).

FIGS. 21-29 present high performance liquid chromatography (HPLC) and thin layer chromatography (TLC) data for samples of a 9-herb composition. The data identifies active ingredients (see Table II and Table III) for certain herbs in the composition.

FIGS. 21 and 22 show HPLC data for icarrin (an active ingredient of *Herba Epimedii*) in a sample of the 9-herb composition and in a standard, respectively. FIGS. 23 and 24 show HPLC data for psoralen (an active ingredient of *Fructus Psoraleae*) in a sample of the 9-herb composition and in a standard, respectively. FIGS. 25 and 26 show HPLC data for schizandrin (an active ingredient of *Fructus Schisandrae Chinensis*) in a sample of the 9-herb composition and in a standard, respectively. FIGS. 27-29 show TLC data for oleanolic acid (an active ingredient of *Fructus Ligustri Lucidi*) in a standard, an extract of the herb *Fructus Ligustri Lucidi*, and a sample of the 9-herb composition, respectively.

Table XI presents the HPLC run data for the presented samples.

TABLE XI

HPLC Run Data

| Sample | Run Time | Peak Height | Peak Area | Conc (%) | Width | Slope |
|---|---|---|---|---|---|---|
| FIG. 21 | 8.023 | 258456.3 | 3717896 | 1.5793 | 35 | 70 |
| FIG. 22 | 8.082 | 570963.0 | 8274640.4 | | 35 | 70 |
| FIG. 23 | 13.682 | 59752.1 | 1380002.9 | 0.3429 | 5 | 50 |
| FIG. 24 | 15.157 | 437600.8 | 12516274.6 | | 5 | 50 |
| FIG. 25 | 12.732 | 8397.6 | 147240.6 | 0.0552 | 5 | 50 |
| FIG. 26 | 12.757 | 420076.6 | 8174213.6 | | 5 | 50 |

Many of the active-described examples have been directed at a 9-herb composition. As noted above, traditional Chinese Medicine focuses on a systemic or holistic approach to treating or preventing ailments. Kidney health represents several aspects including, but not limited to, prostate health, urination frequency, and sexual satisfaction. In addition to treating specific aspects, in one embodiment, the 9-herb composition is suitable for addressing the overall health of the kidney. Other indications for which embodiments of the composition are suitable include tonifying the kidney and benefiting the essence, strengthening muscles and bones, stabilizing sperm, and reducing urination. Still other indications for which embodiments are suitable include waste and joint pain caused by kidney deficiency, chilly limbs and intolerance to cold, dizziness, spermatorrhea and premature ejaculation, and hair loss. Embodiments of the composition also include compositions having less than each of the nine herbal components. Examples include, but are not limited to, compositions including one or more herbal components to treat, for example, a specific aspect of kidney health. In one embodiment, a suitable composition includes Herba epimdii and one or more of the supplemental herbs *Radix Morindae Officinalis, Fructus Rosae Laevigatae, Fructus Rubi, Fructus Schisandrac Chinensis, Fructus Ligustri Lucidi, Semen Cuscutae, Fructus Psoraleae*, and *Radix Astragali*. In another embodiment, the composition includes the active ingredients (identified above) of one or more of the listed herbs. Further, the compositions described may be used in conjunction with other compositions (e.g., medicaments) in the treatment of various kidney disorders or the promotion of kidney health. For example, the composition described may be used in conjunction with a daily multivitamin. Alternatively, in the treatment of prostate cancer, for example, the composition may be combined with an anti-inflammatory agent that may further reduce PSA levels or a drug that regulates testosterone production in the body. Finally, the compositions described herein were presented in terms of kidney health. It is appreciated that the compositions described may have benefits beyond kidney health or treating kidney disorders and find uses in these various areas. Representative examples, include, but are not limited to, the treatment of various other cancers.

While compositions and methods have been described in terms of preferred embodiments, it will be apparent to those of skill in the art that variations may be applied to the compositions and methods described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method comprising:
   identifying a human with a kidney disorder; and
   establishing a regimen for administering a composition to the human, the composition formulated to restore stasis in the kidney comprising:
   an aliquot of the herb *Herba Epimedii*, and
   an aliquot of *Fructus Rosae Laevigatae, Fructus Rubi, Fructus Psoralea, Radix Morindae Officinalis, Fructus Schisandrac Chinensis, Fructus Ligustri Lucidi, Semen Cuscutae*, and *Radix Astragali*.

2. The method of claim 1, wherein the kidney disorder is polyuria.

3. The method of claim 1, wherein the kidney-disorder is incontinence.

4. The method of claim 3, wherein said incontinence is nocturnal incontinence.

5. The method of claim 1, wherein the kidney disorder is proteinuria.

6. A method for treating a kidney disorder comprising:
   administering to a human a composition formulated to restore stasis in the kidney comprising an aliquot of the herb *Herba Epimedii* and an aliquot of *Fructus Rosae Laevigatae, Fructus Rubi, Fructus Psoralea, Radix Morindae Officinalis, Fructus Schisandrac Chinensis, Fructus Ligustri Lucidi, Semen Cuscutae*, and *Radix Astragali*.

7. The method of claim 6, wherein the kidney disorder is polyuria.

8. The method of claim 6, wherein the kidney disorder is incontinence.

9. The method of claim 8, wherein said incontinence is nocturnal incontinence.

10. The method of claim 6, wherein the kidney disorder is proteinuria.

* * * * *

UNITED STATES PATENT AND TRADEMARK OFFICE
CERTIFICATE OF CORRECTION

PATENT NO. : 7,465,466 B2  Page 1 of 1
APPLICATION NO. : 11/053227
DATED : December 16, 2008
INVENTOR(S) : Wen Hsien Chou It is certified that error appears in the above-identified patent and that said Letters Patent is hereby corrected as shown below:

In column 43, claim 3, line 17, delete "kidney-disorder" and insert -- kidney disorder --

Signed and Sealed this

Twenty-second Day of June, 2010

David J. Kappos
*Director of the United States Patent and Trademark Office*